(12) United States Patent
Rotenstreich et al.

(10) Patent No.: US 9,655,509 B2
(45) Date of Patent: May 23, 2017

(54) SYSTEM AND METHOD FOR OBJECTIVE CHROMATIC PERIMETRY ANALYSIS USING PUPILLOMETER

(75) Inventors: Ygal Rotenstreich, Kfar Bilu (IL); Mordecai Rosner, Kiryat Ono (IL)

(73) Assignee: Tel Hashomer Medical Research Infrastructure and Services, Ltd., Ramat Gan (IL)

(*) Notice: Subject to any disclaimer, the term of this patent is extended or adjusted under 35 U.S.C. 154(b) by 252 days.

(21) Appl. No.: 13/388,529

(22) PCT Filed: Aug. 2, 2010

(86) PCT No.: PCT/IL2010/000624
§ 371 (c)(1),
(2), (4) Date: Feb. 2, 2012

(87) PCT Pub. No.: WO2011/016029
PCT Pub. Date: Feb. 10, 2011

(65) Prior Publication Data
US 2012/0127430 A1 May 24, 2012

Related U.S. Application Data

(60) Provisional application No. 61/230,733, filed on Aug. 2, 2009.

(51) Int. Cl.
*A61B 3/14* (2006.01)
*A61B 3/10* (2006.01)
*A61B 3/02* (2006.01)
*A61B 3/00* (2006.01)
*A61B 3/024* (2006.01)
*A61B 3/11* (2006.01)

(52) U.S. Cl.
CPC .............. *A61B 3/024* (2013.01); *A61B 3/112* (2013.01)

(58) Field of Classification Search
CPC .. A61B 3/00; A61B 3/103; A61B 3/02; A61B 3/113; A61B 3/1015; A61B 3/1225; A61B 3/111; A61B 3/08; A61B 3/0285; A61B 3/1208; A61B 3/032; A61B 3/024; G02C 13/005
USPC ....... 351/200, 202, 205, 221, 246, 210, 204, 351/201, 209, 211, 218, 222–226
See application file for complete search history.

(56) References Cited

U.S. PATENT DOCUMENTS

| 5,114,222 A | 5/1992 | Cornsweet |
| 5,422,690 A | 6/1995 | Rothberg et al. |

(Continued)

FOREIGN PATENT DOCUMENTS

| EP | 1 790 281 A1 | 5/2007 |
| JP | 2004216118 A | 8/2004 |

OTHER PUBLICATIONS

Gomez, E. et al.; "Pupillary Escape Quantification with an Image-Processing System in Clinical Perimetry"; Bioelectronics Section, Department of Electrical Engineering; Proceeding of SPIE vol. 2673; 1996; pp. 252-261.

(Continued)

*Primary Examiner* — Dawayne A Pinkney
(74) *Attorney, Agent, or Firm* — Dinsmore & Shohl LLP

(57) ABSTRACT

The present invention relates to a system, device and a method for objective visual field testing and in particular, to such a system and method in which provides objective chromatic perimetry test or color vision test using a pupillometer.

29 Claims, 15 Drawing Sheets

(56) References Cited

U.S. PATENT DOCUMENTS

| | | | |
|---|---|---|---|
| 5,459,536 A * | 10/1995 | Shalon | A61B 3/0083 351/222 |
| 5,610,673 A | 3/1997 | Rafal et al. | |
| 5,805,271 A | 9/1998 | Kirschbaum et al. | |
| 6,022,109 A | 2/2000 | Dal Santo | |
| 6,116,736 A | 9/2000 | Stark et al. | |
| 6,260,968 B1 | 7/2001 | Stark et al. | |
| 6,820,979 B1 | 11/2004 | Stark et al. | |
| 7,083,280 B2 | 8/2006 | Hakamata | |
| 7,118,217 B2 | 10/2006 | Kardon et al. | |
| 7,147,327 B2 | 12/2006 | Stark et al. | |
| 7,216,982 B2 | 5/2007 | Fujimatsu et al. | |
| 7,407,287 B2 | 8/2008 | Hakamata | |
| 7,448,751 B2 | 11/2008 | Kiderman et al. | |
| 7,520,614 B2 | 4/2009 | Joos et al. | |
| 7,614,746 B2 | 11/2009 | Severns | |
| 7,625,087 B2 | 12/2009 | Taylor et al. | |
| 7,665,845 B2 | 2/2010 | Kiderman et al. | |
| 7,670,002 B2 | 3/2010 | Stark et al. | |
| 7,677,728 B2 | 3/2010 | Hirohara et al. | |
| 7,712,899 B2 | 5/2010 | Tanassi et al. | |
| 7,731,360 B2 | 6/2010 | MacDougall et al. | |
| 7,753,523 B2 | 7/2010 | Kiderman et al. | |
| 7,866,818 B2 | 1/2011 | Schroeder et al. | |
| 7,967,442 B2 | 6/2011 | Siminou | |
| 7,976,160 B2 | 7/2011 | Nauche | |
| 7,980,699 B2 | 7/2011 | Neal et al. | |
| 8,016,420 B2 | 9/2011 | Yee et al. | |
| 8,096,658 B2 | 1/2012 | Kikawa et al. | |
| 8,235,526 B2 | 8/2012 | Stark et al. | |
| 8,348,426 B2 | 1/2013 | Tsukada et al. | |
| 8,388,135 B2 | 3/2013 | Hacker et al. | |
| 8,393,734 B2 | 3/2013 | Privitera et al. | |
| 8,500,281 B2 | 8/2013 | Ahn et al. | |
| 8,534,840 B2 | 9/2013 | Siminou | |
| 8,662,667 B2 | 3/2014 | Schuhrke et al. | |
| 8,744,140 B2 | 6/2014 | Baughman et al. | |
| 8,750,575 B2 | 6/2014 | Baughman et al. | |
| 8,807,753 B2 | 8/2014 | Maddess et al. | |
| 8,833,940 B2 | 9/2014 | Yee et al. | |
| 8,911,085 B2 | 12/2014 | Privitera et al. | |
| 9,101,296 B2 | 8/2015 | Schroeder et al. | |
| 9,198,570 B2 | 12/2015 | Siminou, III et al. | |
| 9,220,408 B2 | 12/2015 | Privitera et al. | |
| 2002/0099305 A1 * | 7/2002 | Fukushima et al. | 600/558 |
| 2003/0098951 A1 | 5/2003 | Hakamata | |
| 2004/0246441 A1 | 12/2004 | Stark et al. | |
| 2005/0099601 A1 | 5/2005 | MacDougall et al. | |
| 2005/0270483 A1 | 12/2005 | Fujimatsu et al. | |
| 2006/0106437 A1 * | 5/2006 | Czeisler et al. | 607/88 |
| 2006/0181678 A1 | 8/2006 | Stark et al. | |
| 2006/0181679 A1 | 8/2006 | Hakamata | |
| 2006/0189886 A1 | 8/2006 | Jones et al. | |
| 2007/0121068 A1 | 5/2007 | MacDougall et al. | |
| 2007/0132841 A1 | 6/2007 | MacDougall et al. | |
| 2007/0229760 A1 | 10/2007 | Hirohara | |
| 2008/0024724 A1 * | 1/2008 | Todd | 351/222 |
| 2008/0049186 A1 | 2/2008 | MacDougall et al. | |
| 2008/0049187 A1 | 2/2008 | Joos et al. | |
| 2008/0117384 A1 * | 5/2008 | Inakagata et al. | 351/243 |
| 2008/0198330 A1 | 8/2008 | Taylor | |
| 2008/0234972 A1 | 9/2008 | Tsukada et al. | |
| 2008/0273084 A1 | 11/2008 | MacDougall et al. | |
| 2008/0278685 A1 | 11/2008 | MacDougall et al. | |
| 2008/0284979 A1 | 11/2008 | Yee et al. | |
| 2009/0161090 A1 * | 6/2009 | Campbell | A61B 3/0091 356/3 |
| 2009/0174865 A1 * | 7/2009 | Privitera et al. | 351/246 |
| 2009/0190093 A1 | 7/2009 | Tanassi et al. | |
| 2010/0149489 A1 | 6/2010 | Kikawa et al. | |
| 2010/0165293 A1 | 7/2010 | Tanassi et al. | |
| 2010/0195049 A1 | 8/2010 | Stark et al. | |
| 2010/0214532 A1 | 8/2010 | Siminou | |
| 2010/0220286 A1 | 9/2010 | Nauche | |
| 2010/0249532 A1 * | 9/2010 | Maddess et al. | 600/300 |
| 2011/0033090 A1 | 2/2011 | Baughman et al. | |
| 2011/0043758 A1 | 2/2011 | Ahn et al. | |
| 2011/0069279 A1 | 3/2011 | Hacker et al. | |
| 2011/0228224 A1 | 9/2011 | Siminou | |
| 2011/0279777 A1 | 11/2011 | Yee et al. | |
| 2012/0268715 A1 | 10/2012 | Stark et al. | |
| 2012/0274906 A1 | 11/2012 | Privitera et al. | |
| 2013/0011023 A1 | 1/2013 | Baughman et al. | |
| 2013/0033677 A1 | 2/2013 | MacDougall et al. | |
| 2014/0043587 A1 | 2/2014 | Siminou, III et al. | |
| 2014/0347629 A1 | 11/2014 | Donitzky et al. | |
| 2015/0282704 A1 | 10/2015 | Maddess et al. | |
| 2015/0297074 A1 | 10/2015 | Privitera et al. | |
| 2015/0342495 A1 | 12/2015 | Davis et al. | |

OTHER PUBLICATIONS

Tapia, J. et al.; "Pupillary Responses Evoked by Chromatic Stimulus in Objective Perimetry"; Electrical Engineering Department, Bioelectronics Section; IS&T/SPIE Conference on Human Vision and Electronic Imaging IV; SPIE vol. 3644; Jan. 1999; pp. 598-605.

Rotenstreich, Y. et al.; "The Application of Chromatic Dark-Adapted Kinetic Perimetry to Retinal Diseases"; Department of Ophthalmology and Visual Sciences; Ophthalmology, Jun. 2004; vol. 111; No. 6.; pp. 1222-1227.

Maeda, F. et al.; "A Pupil Perimeter for Objective Visual Field Measurement"; Department of Sensory Science; Complex Medical Engineering, May 2007; IEEE/ICME International Conference; pp. 1116-1119.

International Search Report and Written Opinion; Mailed Mar. 23, 2011 for corresponding PCT Application No. PCT/IL2010/000624.

European Search Report; Mailed Feb. 26, 2015 for the corresponding EP Application No. 10754996.6.

Tapia et al., "Pupillary responses evoked by chromatic stimulus in objective perimetry", IS&T/SPIE Conference on Human Vision and Electronic Imaging IV, Jan. 1999, 598-605, SPIE vol. 3644.

Curcio et al., "Human Photoreceptor Topography", The Journal of Comparative Neurology, 1990, 292: 497-523, Wiley-Liss, Inc.

Kardon et al., "Chromatic Pupillometry in Patients with Retinitis Pigmentosa", American Academy of Opthalmology, 2011, 376-381, Elsevier Inc.

Kardon et al., "Chromatic Pupil Responses. Preferential Activation of the MelanpsinMediated Versus Outer Photoreceptor-Mediated Pupil Light Reflex", American Academy of Ophthalmology, 2009, 1564-1573.

Rotenstreich et al., "The Application of Chromatic Dark-Adapted Kinetic Perimetry to Retinal Diseases", American Academy of Ophthalmology, 2004, 1222-1227, Elsevier Inc.

* cited by examiner

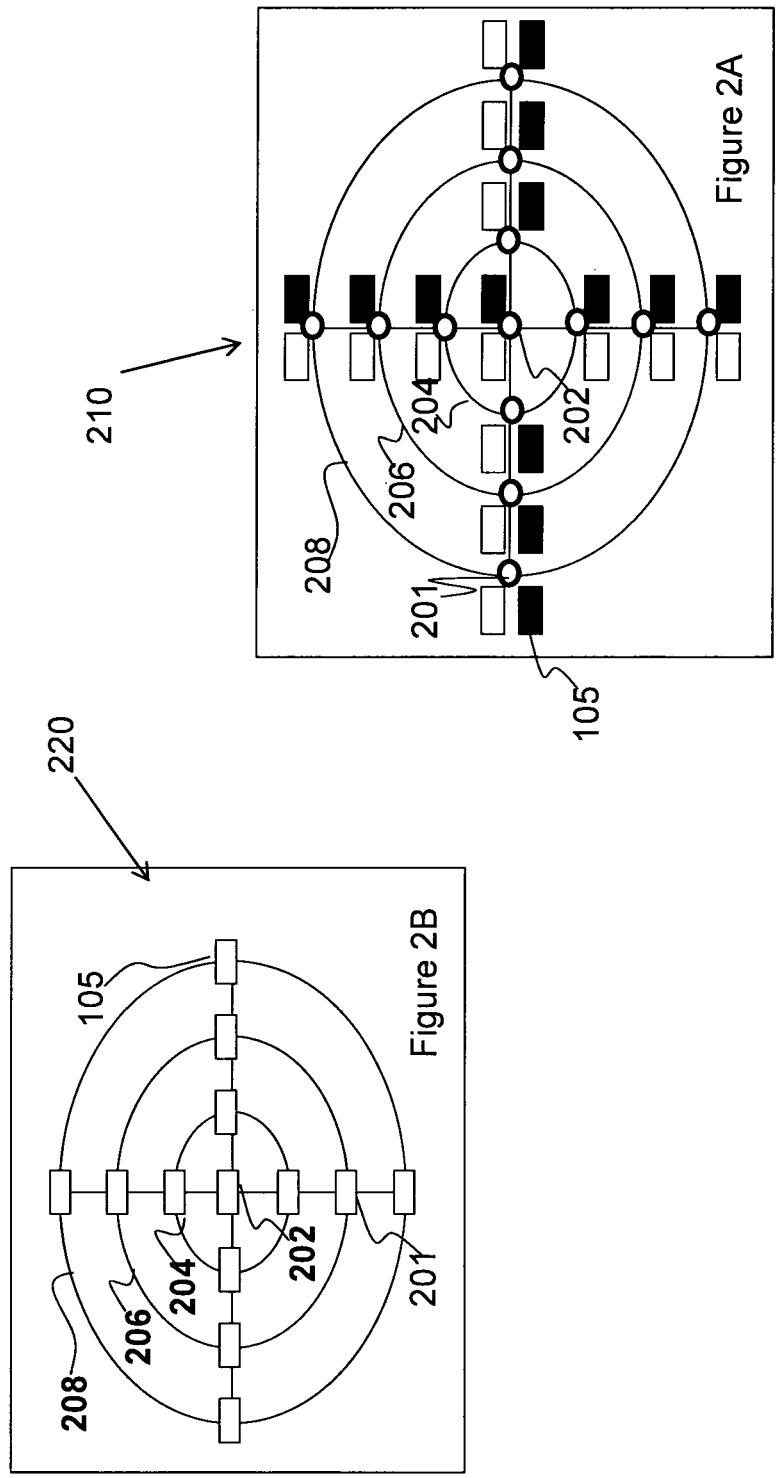

SYSTEM AND METHOD FOR OBJECTIVE CHROMATIC PERIMETRY ANALYSIS USING PUPILLOMETER

CROSS-REFERENCE TO RELATED APPLICATIONS

This is a national-stage application of PCT/IL2010/000624, filed on Aug. 2, 2010 and published as WO2011/016029, which claims the benefit of the filing date of U.S. provisional application No. 61/230,733, filed on Aug. 2, 2009, the teachings of both of which are incorporated herein by reference.

FIELD OF THE INVENTION

The present invention relates to a system, device and a method for visual field testing and in particular, to such a system and method in which provides objective chromatic perimetry test or color vision test using a pupillometer.

BACKGROUND OF THE INVENTION

A visual field test also known as perimetry, is a method of measuring an individual's entire scope of vision that is, the central and peripheral vision. Such visual field tests attempt to map the visual field of each eye individually. Visual field testing is most frequently used to detect any signs of glaucoma caused damage to the optic nerve. In addition it is useful for detection of central or peripheral retinal disease, eyelid conditions such as ptosis or drooping, optic nerve disease, and diseases affecting the visual pathways within the brain and associated with the Central Nervous System ("CNS").

The present prevailing method for visual field testing is performed as follows: one eye of the patient is covered and the chin is placed on a concave chin rest. The patient must look straight ahead at all times in order to avoid testing the central vision rather than the periphery. Next, light flashes of various intensities and locations are projected on the tested eye. Whenever the patient notices a flash he has to push a button. After all the relevant looking angles are covered a computer program analyzes the patient's responses and assesses the visual field map of the tested eye.

The principal stumbling block of the above procedure is its subjectivity, requiring the patient to understand the testing instructions, fully cooperate, and complete the entire test in order to provide useful information. However, the patient cooperation may strongly depend on his level of fatigue, wakefulness and attentiveness. This problem is especially severe in case of ill or elderly patients, younger children or patients with mental disabilities and developmental delay. Consequently, the test results obtained by the current method may not be accurate and may lead to false medical diagnosis. Moreover, the results may not be repeatable, which does not allow for reliable and effective tracking of the patient's medical condition.

Additional tests to assess the state of the eye is the Pupillary Light Reflex ("PLR") to provide clinical signs of the condition associated with the CNS. The PLR test the pupil response, namely constriction, by testing the pupil's stimulus response in each eye where a healthy eye is indicative of symmetric constriction of both pupils. A quantitative measurement of a PLR may be obtained using a pupillometer.

Pupil perimetry utilizes a pupillometer together with a stimulus arrangement similar to that of a perimeter to measures the latency and amplitude of the constriction of the pupil in response to a stimuli, usually in the form of a spot ("small-area") flashes of light that is directed to different locations on the retina.

The pupillary response to spatially-localized luminance increments has been used as an indicator of glaucomatous retinal damage, but the small-area stimuli used in pupil perimetry may target small retinal areas that only weakly stimulate a PLR, and may fail to stimulate a PLR if the small retinal area that is being stimulated by light has been damaged by glaucoma. Standard pupil perimetry testing produce large variations in pupil response amplitude among patients and the changes in sensitivity of the pupil response with the retinal location of the small-area light stimulus have also limited the usefulness of such measurements.

Pupillometer based objective visual tests have been recited in some references, based on an achromatic beam stimulus which is applied at various angles, for example U.S. Pat. No. 5,610,673 to Rafal et al, U.S. Pat. No. 7,524,064 to Wyatt, U.S. Pat. No. 7,258,444 to Gorin. However, these methods fail to achieve neither accurate nor repeatable visual field mapping due to its susceptibility to time variations in the human ocular system and to differences in the behavior of the ocular system of different patients.

SUMMARY OF THE INVENTION

There is an unmet need for, and it would be highly useful to have, a system and a method for objective chromatic perimetry analysis using pupillometer that is adept at providing an indication of the state of health of the eye and in particular identifying damage to the eye. The present invention overcomes the deficiencies of the background by providing a system and method that provides an objective test and analysis that is able to quantify an individual's state of health of the eye. The system and method overcome the deficiencies of the art by providing individual specific indication of problem areas of the eye in obtaining measurements that are relative to an individual's field of vision at specific visual field testing points, rather than full field test provided by the prior art. Moreover the objective test of optional embodiments of the present invention provides for a quick test that does not require patient specific interaction or input, that is subjective and often unreliable or misleading. Rather the test of the present invention most preferably measures a subject's PLR without a subject's input ensuring the objective nature of the test, hence more reliable and repetitive.

An optional embodiment of the present invention provides a system and method for testing an individual's response to at least two or more stimuli that are individually associated with the anatomical tissue, cells, ganglion, or the like anatomical structures comprising the eye, for example including but not limited to ganglion, most preferably the rods and cones, and elucidating a ratio reflective of the relative response of the stimuli utilized. For example the ratio utilized may comprise at least two response measurements associated with the group comprising of rods, cones, ganglion in any combination thereof, therein providing for a ratio selected from the group consisting of rods to cones; rods to ganglion, cones to ganglion, or the like.

An optional embodiment of the present invention provides a system and method for testing an individual's response to at least three or more stimuli that are individually associated with the anatomical tissue, cells, ganglion, or the like anatomical structures comprising the eye, for example including but not limited to ganglion, rods and cones, and optionally elucidating at least one or more ratio reflective of the relative response of the stimuli utilized; more preferably elucidating at least two ratios reflective of the relative response of the stimuli utilized. For example, at least two ratios utilized may for example be any combination of the ratio selected from the group comprising rods to ganglion, cones to ganglion, rods to cone, ganglion to rods, ganglion to cones, or the like. Optionally the evaluation of the eye may be provided by a utilizing a ratio comprising a common denominator for example, a ratio of rods to ganglion may be compared and evaluated with respect to the ratio of cones to ganglion.

A preferred embodiment of the present invention introduces at least two or more stimuli comprising at least one cone specific stimulus and at least one rod specific stimulus, to a plurality of location herein referred to as the visual field points ('VFP') of at least one eye, and measuring the PLR response, namely pupil constriction, via a pupillometer; and comparing the PLR response, at a given VFP, of the respective stimulus to obtain a ratio indicative an individual's state of health of the eye.

For example, stimulus that is geared toward the rod and stimulus is provided in the form of chromatic light flashes comprising a short wavelength most preferably a narrow beam within the blue spectrum range, for example including but not limited to wavelength of about 450 nm, 455 nm, 460 nm, 465 nm, 470 nm, 475 nm, 480 nm, 485 nm, 490 nm or the like, most preferably the stimuli utilized is about 485 nm.

Optionally the cone specific stimulus is provided in the form of chromatic light flashes comprising a long wavelength most preferably narrow beam within the red spectrum range, for example including but not limited to wavelength of about 630 nm, 635 nm, 640 nm, 645 nm, 650 nm, 655 nm, 660 nm, 665 nm, 670 nm, 675 nm, 680 nm, 685 nm, 690 nm, 695 nm, 700 nm any combination thereof or the like.

Optionally and preferably the ratio obtained according to optional embodiment of the present invention is a ratio of cone specific stimulus response to a rod specific stimulus response.

Optionally the ratio utilized may be region specific about the different visual field points tested. For example, the central field points of the VFP may optionally utilize a ratio determined by rod specific stimulus response to cone specific stimulus response, while the peripheral field points may utilize a ratio of cone specific stimulus response to a rod specific stimulus response, as an indication of eyes state of health in the particular region and/or visual field point.

Optionally the ratio provided by the system and method of the present invention provides for individual specific measurements, reduce variability between the tested population, an indicator of an individual's internal state of balance associated with the sympathetic and parasympathetic state. Optionally utilization of the ratio accounts for and reduces variability due to light scattering and supranuclear inhibition. Optionally the ratio according to the present invention may account for the variability among the population pupil size, therein providing a standardized measurement relative to an individual rather than a population. Optionally and preferably the ratio is adept at assessing and providing an indication of the extent of an individual's visual field rim.

The present invention resolves the above background art limitations by providing, in at least some embodiments, a reliable and objective visual field testing, that is reliable and repeatable.

An optional embodiment of the present invention provides a decision support system for diagnosing eye and/or retinal damage by assessing a subject's PLR in response to at least two or more chromatic stimuli to define a ratio indicative of the underlying state of health of the tested eye.

Optionally the at least two stimuli is composed of a first stimulus comprising a short wavelength chromatic stimulus and a second stimulus comprising a long wavelength chromatic stimulus, and wherein the ratio is the determined by evaluating the long wavelength PLR response with respect to the short wavelength PLR response of the tested eye.

Optionally the first stimulus is within the blue range from about 450 nm to about 490 nm, optionally and preferably about 475 nm, more preferably 480 nm and most preferably 485 nm. Optionally the second stimulus is within the red range from about 635 nm to about 700 nm, optionally and preferably about 650 nm.

An optional embodiment of the present invention provides a system for objective chromatic perimetry test comprising a pupillometer, a process and a camera that most preferably does not require subject input:

a. the pupillometer comprising:

i. a testing compartment provided in the form of a hemispheric bowl, wherein an inner surface of the bowl comprises a plurality of openings forming form a plurality of visual field testing points; and ii. wherein the hemispheric bowl may be associated with a plurality of chromatic beam emitters arranged about the visual field such that they are disposed over the plurality of visual field testing points; and wherein the chromatic emitters provide for generating a chromatic stimuli about the visual field points; and wherein iii. the stimuli comprises at least two different stimulus selected from the visual spectrum spanning from about 390 nm to about 750 nm wherein the different stimulus are individually characterized by their individual stimulus parameters including wavelength, duration, delay, and intensity; and iv. wherein the outer perimeter of the inner surface of the testing compartment further comprises a light adaptation emitter wherein the adaptation emitter comprising at least one or more chromatic beam emitters; and v. The inner surface further comprising a fixation point opposite a subject's line of sight; and vi. The bowl further comprising at least one or more opening for at least one or more camera provided for recording the pupil contraction in response to the stimuli; and b. The processor provided for controlling the chromatic beam emitters, the stimulus parameters and the visual field points; and wherein the processor processes data associated with and generated by the stimulus and camera.

Optionally and preferably the device according to the present invention may be adapted to provide for color vision testing.

Optionally the stimuli may include a first stimulus characterized in that it may be a short wavelength chromatic beam and a second stimulus characterized in that it may be a long wavelength chromatic beam.

Optionally the stimuli comprises up to three individual stimulus. Optionally the first stimulus may be provided in the form of a chromatic beam in the blue wavelength range centered at about 480 nm or about 485 nm. Optionally the chromatic beam stimulus may be selected from about 450 nm to about 495 nm comprises a blue wavelength beam selected from about the group consisting of about 450 nm, 455 nm, 460 nm, 465 nm, 470 nm, 475 nm, 480 nm, 485 nm, 490 nm, 495 nm, 500 nm or any combination thereof.

Optionally the second stimulus may be a chromatic beam in the red wavelength range centered at about 640 nm or about 620 nm. Optionally the second stimulus chromatic beam may be selected from about 590 nm to about 750 nm and comprising red wavelength selected from the group for example including but not limited to about 610 nm, 615 nm, 620 nm, 625 nm, 630 nm, 635 nm, 640 nm, 645 nm, 650 nm, 655 nm, 660 nm, or any combination thereof.

Optionally the first stimulus and the second stimulus are adapted to individually stimulate a specific anatomical structure of the eye. Optionally the first stimulus may be adapted to stimulate rods and ganglion while the second stimulus may be adapted to stimulate cones.

An optionally the stimulus may be characterized in that it may be specific an anatomy of the eye; and wherein the system of the present invention comprises at least two stimuli that may be generated to simulate at least two anatomical structures of the eye.

Optionally a light adaptation emitter comprises three chromatic beam emitters adapted to produce a visible color about the inner surface of the bowl of the test compartment.

Optionally the hemispheric bowl may be provided in the form of a ganzfeld dome or a Goldmann, or static perimeters.

Optionally the plurality of chromatic beam emitters or the plurality of openings are further provided with a controllable shutter for controlling the size and shape of the generated stimulus. Optionally and preferably the shutter size may be adapted to provide a stimulus having a substantially circular formation with a diameter from about 0.8 cm to about 2 cm. Optionally and preferably shutters may be controllable with the processors.

Optionally the plurality of chromatic beam emitters are provided in the form of a Light Emitting Diode ('LED'). Optionally the LED provides a specific chromatic beam characterized in that it may be specific to an anatomy of the eye. Optionally the LED may provide a plurality of optional specific chromatic beams characterized in that each beam may be individually specific to an anatomy of the eye.

Optionally the chromatic beam emitters or the openings about the inner surface of the test compartment are arranged to provide from about 13 to about 256 visual filed testing points about the vertical and horizontal planes of the hemispheric bowl. Optionally each of the visual field point comprises at least one chromatic beam emitters in the form of a LED that may provide a plurality of optional specific chromatic beams.

Optionally the device according to the present invention may be configured such that each of the visual field points may comprise at least two chromatic beam emitters in the form of a LED characterized in that each LED provides a specific chromatic beam.

Optionally the device according to the present invention may be configured such that each of the visual field point comprises at least three chromatic beam emitters that may optionally be provided in the form of a LED.

Optionally the chromatic beams may be further characterized in that each beam may be individually specific to an anatomic structure of the eye, for example including but not limited to the rods and cones, ganglion.

Optionally the fixation point may be disposed at about the pole of the hemispheric bowl and may comprise up to four fixation points about the center.

Optionally the system according to the present invention may comprise at least one and up to four cameras, for objectively recording the PLR of subject. Optionally the system may comprise at least one, or at least two, or at least three or at least four cameras. Optionally the PLR may be recorded for each eye utilizing at least two cameras.

Optionally the shutter may for example be provided in the form of a static shutter or a dynamic shutter, or a combination thereof or the like.

Optionally the stimulus duration or delay may be controllably set to be any single value or range of values selected from about 100 ms to about 4000 ms.

Optionally the stimulus intensity used with the system and method according got the present invention may be controllably set to be any single value or range of values from about from $3.98 \times 10^{-8}$ cd/m$^2$ up to about $3.98 \times 10^2$ cd/m$^2$.

An optional embodiment of the present invention provides for a method for determining the state of health of an eye with a pupillometer providing an objective chromatic perimetry analysis test, where most preferably a subject's input is not required and therefore the test is preformed and results are analyzed independently of subject's input. Most preferably the a measurement of the PLR in response to chromatic beam stimuli is presented at a plurality of visual field testing points, and defining a ratio of the measured PLR at each of the plurality of visual field testing points in response to a first chromatic beam stimulus relative to a response to a second chromatic beam stimulus, wherein the first and second stimulus are characterized by parameters for example including but not limited to wavelength, duration, delay, and intensity; and wherein the stimuli wavelength are selected from the visual spectrum spanning from about 390 nm to about 750 nm.

Optionally the first chromatic beam stimulus may be a short wavelength beam and the second chromatic beam stimulus may be a long wavelength beam. Optionally the first chromatic beam may be within the blue wavelength spectrum range centered at about 480 nm or about 485 nm; and the second chromatic beam may be a chromatic beam within the red wavelength spectrum range centered at about 640 nm or about 620 nm.

Optionally the ratio of the PLR measured with the long wavelength response relative to the PLR measured with the short wavelength response. Optionally the first and second chromatic beam stimuli are specific to different anatomical structure within the eye, for example including but not limited to rods, cones and ganglion. Optionally the first stimuli may be directed at the rods; and the second stimuli may be directed at the cones.

Optionally the first stimulus may be provided for a duration of about 1 s (one second), with an intensity of about $3.98 \times 10^{-8}$ cd/m$^2$, with an inter-stimulus pause of about 891 ms (milliseconds); and the second stimulus may be provided for a duration of about 1 s (one second), with an intensity of about $3.98 \times 10^{-8}$ cd/m$^2$, with an inter-stimulus pause of about 1023 ms (milliseconds).

Optionally the first and second stimulus may be presented to a subject at least once and up to three time for each visual field testing point.

Most preferably the ratio may be mapped to a visual field map. Optionally and preferably the ratio or map thereof may be indicative of the state of health of anatomical structures correlated with individual visual field points.

Optionally the ratio that may be indicative of underlying normal and/or healthy anatomical structures are provided by the following field point coordinates and expected ratio (0°, nasal, 0.50); (10°, nasal, 0.41); (10°, temporal, 0.45); (10°, up, 0.48); (10°, down, 0.43); (20°, nasal, 0.40); (20°, temporal, 0.33); (20°, up, 0.38); (20°, down, 0.39); (30°, nasal, 0.50); (30°, temporal, 0.44); (30°, up, 0.5); (30°, down, 0.40). Optionally the ratios may be indicative of the state of health of an eye associated with glaucoma, and retinitis pigmentosa (RP). Optionally the ratios may be indicative of the state of health of an eye associated with color blindness.

Optionally and preferably the test according to the present invention may be performed with background luminance providing for light adaptation. Optionally and preferably background luminance and light adaptation may be controllable, preferably provided to facilitate testing of an anatomical structure of the eye. Optionally the background luminance may be any one value or a range of values selected from about 1 cd/m² to about 20 cd/m². Optionally background luminance may be about 2.7 cd/m² or about 17.1 cd/m² (about 5 foot-lambert). Optionally the onset of light adaptation may be controlled and therefore provided at a plurality of optional portions of the test or at different controllable periods of the test, for example including but not limited to between stimulus presentations, between visual field testing points, between visual field rings, or any combination thereof or the like.

An optional embodiment of the present invention provides device in the form of a pupillometer for performing an objective chromatic perimetry test, that most preferably does not require a subject's input, the device comprising a pupillometer testing compartment and at least one or more camera, the pupillometer testing compartment comprising:

a. the testing compartment provided in the form of a hemispheric bowl, wherein an inner surface of the bowl comprises a plurality of openings forming form a plurality of visual field testing points; and b. wherein the hemispheric bowl may be associated with a plurality of chromatic beam emitters arranged about the visual field such that they are disposed over the plurality of visual field testing points; and wherein the chromatic emitters provide for generating a chromatic stimuli about the visual field points; and wherein c. the stimuli comprises at least two different stimulus selected from the visual spectrum spanning from about 390 nm to about 750 nm wherein the different stimulus are individually characterized by their individual stimulus parameters including wavelength, duration, and intensity; and d. wherein the outer perimeter of the inner surface of the testing compartment further comprises a light adaptation emitter wherein the adaptation emitter comprising at least one or more chromatic beam emitters; and e. The inner surface further comprising a fixation point opposite a subject's line of sight; and f. The bowl further comprising at least one or more opening for at least one or more camera provided for recording the pupil contraction in response to the stimuli.

An optional embodiment of the present invention provides for determining the a ratio of the PLR response at individual visual field testing points based on a response to at least two or more, or three or more, or four or more chromatic beam stimuli presented to a tested eye. Optionally a different ratio may be determined based on how the eye was stimulated for example each eye individually, both eyes in turn, or both eyes simultaneously.

Unless otherwise defined the various embodiment of the present invention may be provided to an end user in a plurality of formats, platforms, and may be outputted to at least one of a computer readable memory, a computer display device, a printout, a computer on a network or a user.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and/or the ability to execute one or more instructions may be described as a computer, including but not limited to a PC (personal computer), a server, a minicomputer, a cellular telephone, a smart phone, a PDA (personal data assistant), a pager. Any two or more of such devices in communication with each other, and/or any computer in communication with any other computer, may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2A-C are a schematic illustrative diagrams of visual field points showing alternative configurations for the chromatic beam emitters according to optional embodiments of the present invention;

FIG. 4A present measured results with the long wavelength stimuli within the red spectrum, about 610 nm, associated with the Cones. FIG. 4B present measured results with the short wavelength stimuli within the blue spectrum, about 485 nm, associated with the Rods. FIG. 4C presents the long wavelength to short wavelength ratio according to the present invention as obtained between the results of FIG. 4A to FIG. 4B.

FIG. 5A present measured results with the long wavelength stimuli within the red spectrum, about 610 nm, associated with the Cones. FIG. 5B present measured results with the short wavelength stimuli within the blue spectrum, about 485 nm, associated with the Rods. FIG. 5C presents the long wavelength to short wavelength ratio according to the present invention as obtained from the results presented in FIG. 5A to FIG. 5B.

FIG. 6A present measured results with the long wavelength stimuli within the red spectrum, about 610 nm, associated with the Cones. FIG. 6B present measured results with the short wavelength stimuli within the blue spectrum, about 485 nm, associated with the Rods. FIG. 6C presents the long wavelength to short wavelength ratio according to the present invention as obtained from the results presented in FIG. 6A to FIG. 6B. FIG. 6D provides an additional view on a background of the traditional visual field map for the tested glaucoma patient.

DESCRIPTION OF THE PREFERRED EMBODIMENTS

The principles and operation of the present invention may be better understood with reference to the drawings and the accompanying description. The following reference labels listed below are used throughout the drawings to refer to objects having similar function, meaning, role, or objective.
100 Pupillometer;
101 Pupillometer test compartment;
102 Pupillometer head and chin support frame;
103 Pupillometer ocular(s);
104 hemispheric surface;
105 chromatic beam emitters;
105a first stimuli chromatic beam emitters;
105b second stimuli chromatic beam emitters;
105c light adaptation RGB emitter;
106 camera;
107 focal fixation point marker;
108 shutters;
109 computer;
110 power supply;
112 light adaptation emitter;
120 objective chromatic perimetry system;
200 visual field map arrangement;
201 visual filed points
202 0° field map ring;
204 10° field map ring;
206 20° field map ring;
208 30° field map ring;
210 multi source chromatic beam emitter configuration;
220 single source chromatic beam emitter configuration.

Figure 1A:
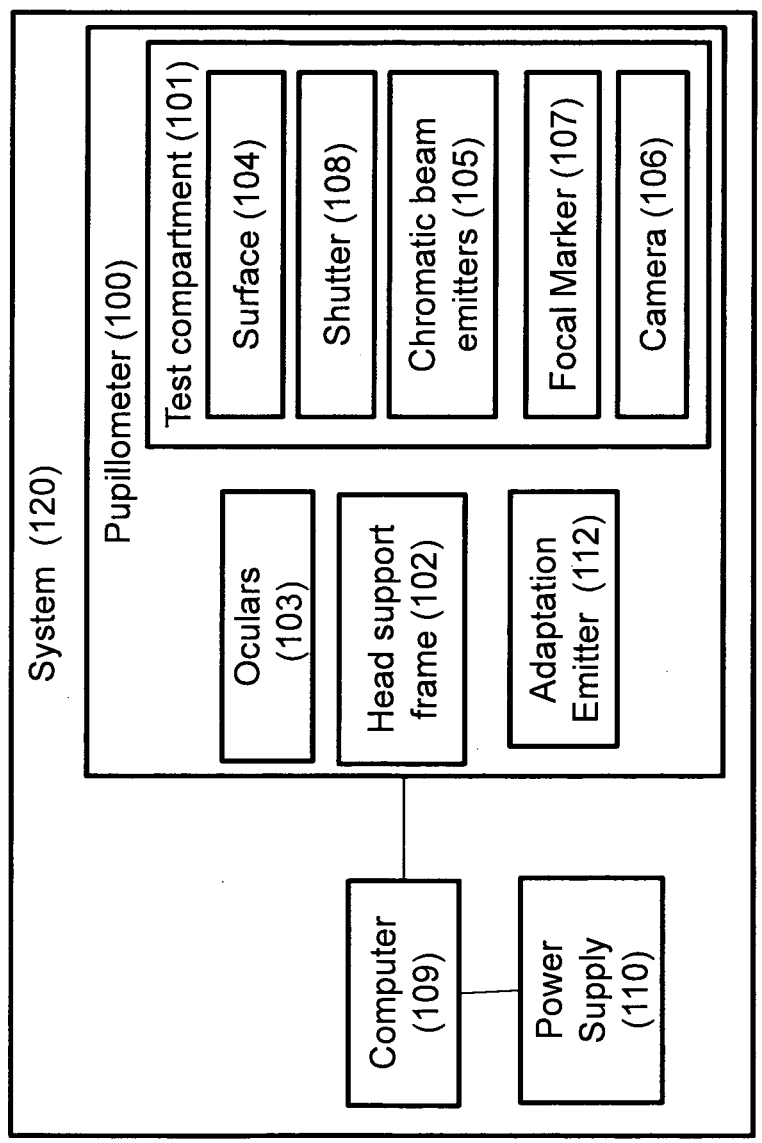
FIG. 1A-B are schematic block diagrams of an exemplary system according to the present invention.
Figure 1B:
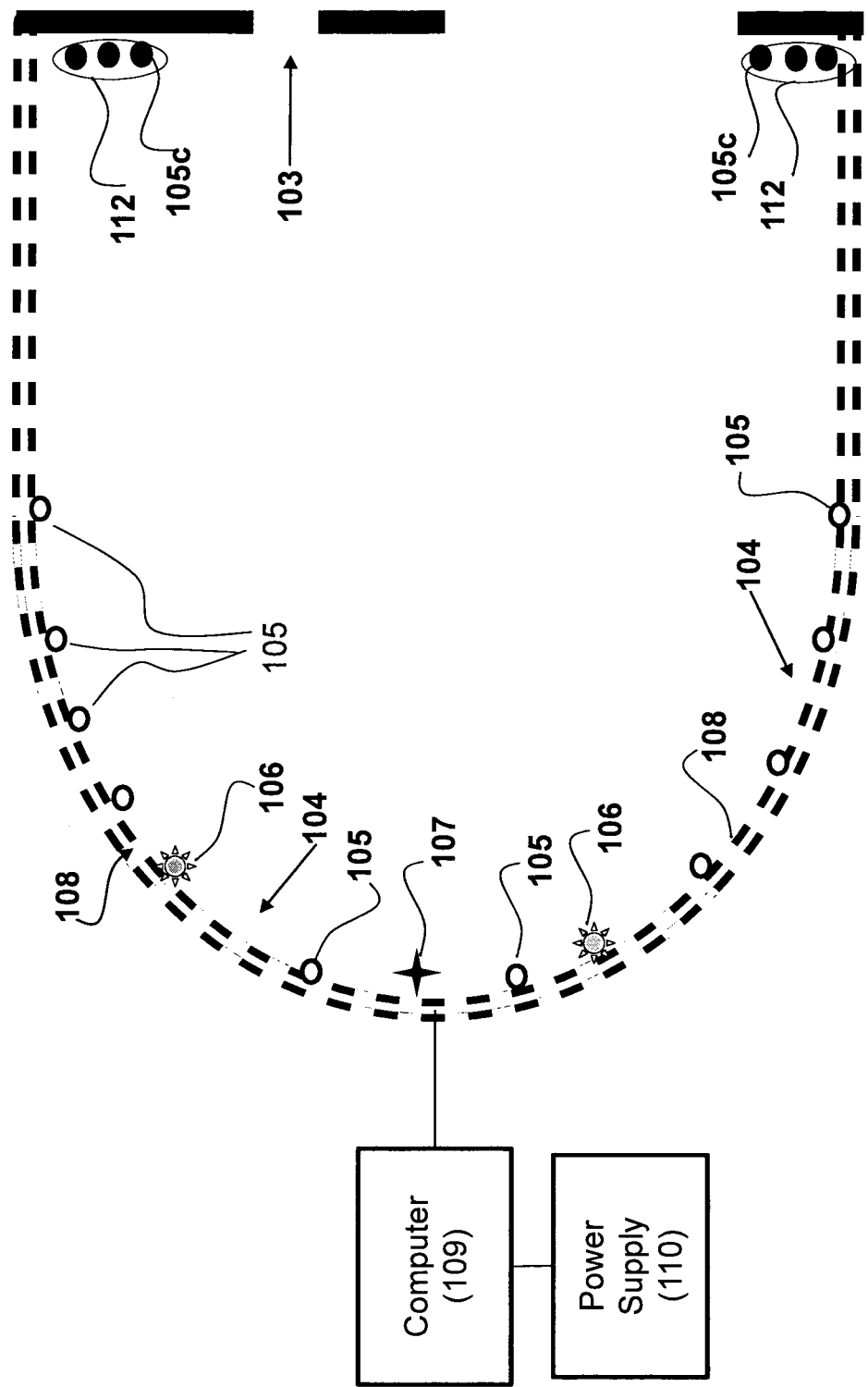

Referring now to the drawings, FIGS. 1A-B show schematic illustrative diagrams of system 120 of the present invention for objective chromatic perimetry analysis comprising a pupillometer 100 and a computer 109. Pupillometer 100 is utilized to perform a Pupillary Light Reflex ("PLR") test of at least one eye where the PLR is measured by presenting the tested eye with stimulus and measuring the pupil's constriction response. Pupillometer 100 comprises a testing compartment 101 most preferably in the form of a Ganzfeld, is a hemispherical shaped bowl to allow for testing of the full visual field of a subject. Preferably testing compartment 101 comprises an inner surface 104 forming a screen onto which the stimuli is presented, a plurality of chromatic beam emitters 105, focal fixation point marker 107 and camera 106.

Test compartment 101 preferably comprises and incorporates and is integrated with inner surface 104, where surface 104 is associated with at least one or more preferably a plurality of chromatic beam emitters 105 that preferably provide for generating and presenting the stimulus for a which a response is measured. Focal fixation point marker 107 provides a subject with a fixation point during the test, optionally and preferably fixation point comprises 4 beams of red light arranged about a central point on surface 104, most preferably the pole of surface 104. Camera 106, for example in the form of a CCD camera or a the like digital camera, may be provided within test compartment and is preferably directed toward the tested eye so as to allow for visualizing and recording the pupil during testing therein providing for recording the PLR of the tested eye. Most preferably at least one camera 106, may be disposed within test compartment 101, optionally at least one and up to four cameras may be provided and arranged within test compartment 101 to better identify the PLR of the tested eye. Optionally two cameras' may be utilized to record a single tested eye. Optionally two cameras may be utilized to record a subject PLR when both eyes are tested simultaneously. Optionally up to four cameras may be utilized to record a subject PLR when both eyes are tested simultaneously, wherein at least one camera and more preferably at least two cameras are provided to record the PLR of each tested eye. Most preferably camera 106 transmits and records the subject's eye during testing sending data to computer 109 or the like processor for analysis, for example including but not limited to a server, PDA, smart phone or the like device comprising a processor. Most preferably data obtained by at least one or more camera 106 is processed with computer 109 via dedicated software.

Optionally camera 106 may be attached, coupled or otherwise associated with surface 104. Most preferably camera 106 continuously captures images of at least one of the tested eye, or of both eyes for example when the consensual reflex is tested. Optionally camera 106 may be substantially simultaneously controlled with emitters 105 by computer 109. Most preferably camera 106 continuously transfers images of the pupil to computer 109 at a rate of about 50 shots-per-second, or 40 shots per second or the like. Optionally the pupillary images may be provided and/or transferred in various forms for example including but not limited to stills, common digital video format or the like as is known in the art. Optionally camera 106 may communicate and/or transfer data to computer 109 through a plurality of optional communication technology and/or protocols for example including but not limited to wired, wireless, cellular, optical or acoustic communication protocols for example including but not limited to infrared, Bluetooth, wifi or the like.

Optionally computer 109 may further provide for a decision support tools associated with the state of health of the eye. Optionally a decision support tool may provide physician and/or clinicians with assistance in analyzing and determining the state of health of the tested eye based on the results obtained with the system and method of embodiments of the present invention.

FIG. 1B provides a cross-section views of an schematic optional test compartment 101 of system 120. Test compartment 101 may be provided as an opaque chamber that preferably serves to block interference of external illumination during testing. Optionally and preferably the front side of test compartment 101 forms a support frame 102 that is capable of receiving the patient's head while supporting the chin and forehead. Preferably the middle section of support frame 102 comprises at least two openings 103 that serve as oculars allowing a subject to view the presented stimulus about surface 104. Optionally and preferably each ocular 103 may be controlled by computer 109. For example when testing only the subject's right eye the right ocular is controllably placed in the open position by computer 109 while the left ocular is placed in the closed position, allowing for isolating the right eye and measuring the PLR of the right eye only.

Figure 2C:
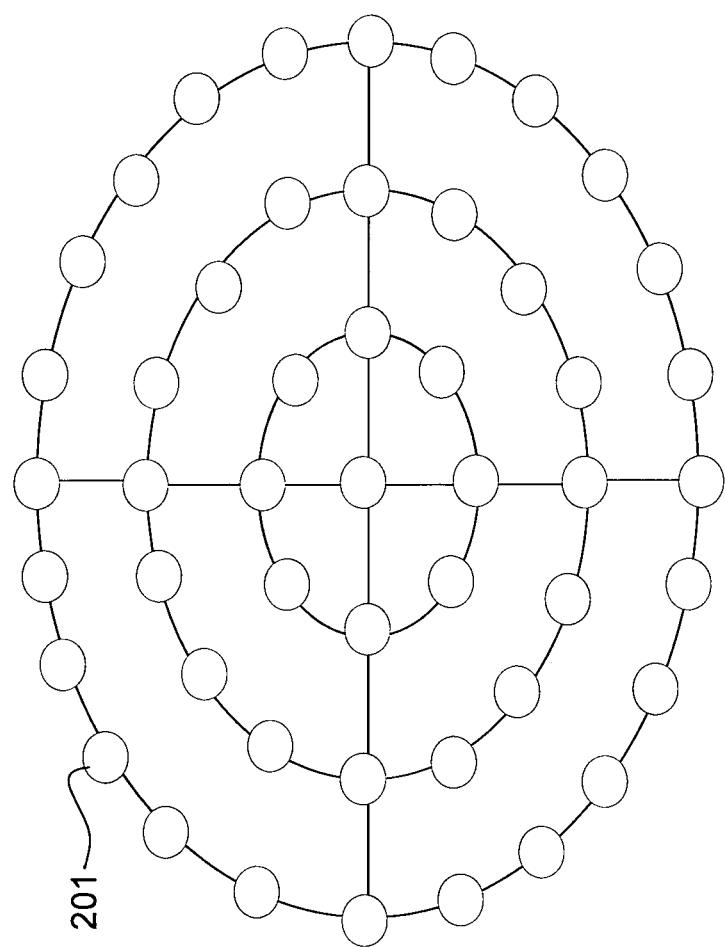

The rear part of testing compartment 101, is optionally and preferably provided in the form of a semispherical bowl, ganzfeld dome, goldmann perimeter or the like surface 104 that is preferably made of a reflective material. Most preferably at least one and more preferably a plurality of chromatic beam emitters 105, optionally in the form of a Light Emitting Diode ('LED') are located about, attached or otherwise coupled to surface 104. Optionally emitters 105 may be integrated with surface 104. Most preferably emitters 105 are provided in the form of a chromatic LED providing a narrow spectrum light source in the visible range. Optionally the arrangement of emitters 105 about surface 104 may be controlled, for example a single multi spectrum LED may be placed about the stimuli location field point as shown in FIG. 2B. Optionally at least two or more preferably a plurality of emitters 105, for example a spectrum specific LED, may be arranged about surface 104 as shown field map 210 in FIG. 2A, wherein each emitter 105 is specific to a particular chromatic stimulus source that is being tested. Most preferably emitters 105 provide for stimulating the tested eye in particular the retina by illuminating a portion of the eye with a chromatic narrow light beam. Optionally emitters 105 may be configured about surface 104 in a dense grid structure, optionally and preferably corresponding to visual field map having a plurality of point being tested, from about 13 to at least 256 or more as show in FIG. 2C. Optionally a plurality of emitters 105 may be associated with or integrated with internal shutters to control stimulus parameters for example the shape, size, timing of the stimulus.

Optionally surface 104 may comprise a plurality of opening and shutters 108 arranged similarly to that of emitters 105 as shown in FIGS. 2A-C, optionally and preferably corresponding to the resolution of the visual field points tested. Optionally shutters 108 and/or openings may be controllable with computer 109 to control at least some parameters of the stimuli presented to the tested eye, for example including parameters such as the shape and size of the stimulus to be provided. Optionally screen 104 may be provided with a finite number, for example three, of controllable opening sizes and or shapes with which the presented stimulus may be controlled. Optionally shutter 108 may provide a stimulus size of bout 0.05 cm to about 2 cm in diameter. For example, the stimulus shape may be chosen from circular with a diameter of about 1 cm, or a square with each side having a length of about 0.95 cm.

Most preferably surface 104 comprises a focal point marker 107 at about the central point of the surface 104. Optionally and preferably marker 107 is provided in the form of a dim red light, that may serve as a focal marker for the tested patient. Optionally the focal fixation point marker may comprise at least one and up to four dim red light source about a central point. During testing a subject is asked to look at focal marker 107 providing a common reference point that is repeatable point for all subjects and/or eyes tested. Optionally at a plurality of focal markers 107 may be utilized with Pupillometer 100.

Optionally light adaptation emitter 112 optionally and preferably comprising at least one and up to three chromatic beam emitters 105c, optionally in the red, green and blue range wavelength, may be disposed about the outer perimeter of test compartment 101 near head support frame 102, for example along the inner surface 104.

Optionally light adaptation emitter 112 may be attached to the front wall of test compartment 101. Preferably when light adaptation emitter 112 is activated it illuminates surface 104 providing for light adaptation as described in stage 302 of FIG. 3 where the light adaptation used may prime particular anatomical structure of the eye therein facilitating the performed test.

Optionally light adaptation emitter 112 may provide for fully illuminating screen 104 in any chromatic wavelength comprising a combination of at least one and up to three chromatic beam emitters 105c. Optionally stimulus control with light adaptation emitter 112 may be provided with controllable shutters 108 to selectively emit the light produced by emitter 112 to select field points 201 corresponding to selected shutters 108 that are in the open position, where most preferably control of the shutter 108 is provided with computer 109. Optionally light adaptation emitter 112 may provide for a color field perimetry test for example for testing color blindness about individual field points as shown in FIG. 2C.

Optionally and preferably computer 109 may provides for overall control of pupillometer 100 and system 120.

Power Supply unit 110 is most preferably coupled with main power which for providing system 120. Preferably power supply 110 converts and/or generates a stabilized DC (Direct Current) voltages that are required for proper operation of system 120 and varying component of pupillometer 100.

FIGS. 2A-B provide illustrative diagrams of a 13 point visual field map 200 showing optional alternative configurations for the chromatic beam emitters 105, for each point 201, in the form of a multi source chromatic beam emitter configuration 210, FIG. 2A, in the form of a single source chromatic beam emitter configuration 220, FIG. 2B, each according to optional embodiments of the present invention.

FIG. 2A shows visual field 210 comprising a plurality of emitters 105 at each visual field points 201, optionally accounting for individual emitter 105, where each emitter 105 may provide for a specific chromatic beam stimulus at the a given visual field point about visual field 210, at each point 201. Optionally at least two or more chromatic beam emitters 105 may be provided at each visual field point 201. For example emitters 105a and 105b may be provided to stimulate the tested eye at the same visual field point, for example at 30° field map ring 208. For example beam emitter 105a may provides a short wavelength chromatic stimulus, for example in the blue range at about 475 nm, while emitter 105b may provide a long wavelength chromatic stimulus, for example in the red range at about 650 nm.

FIG. 2B shows visual field 220 comprising a single emitter 105 at individual visual field points 201, where optionally emitter 105 may provide at least two or more preferably a plurality of optional chromatic beams at varying wavelengths. For example a single beam emitter 105 may provides both a short wavelength chromatic stimulus in the blue range, for example about 475 nm, and a long wavelength chromatic stimulus in the red range, for example about 650 nm, at a given visual field point 201 about visual field 220, for example at 20° field map ring 206, as shown.

FIG. 2C provides a depiction of an optional map of a visual filed map with a plurality of points that may be used to stimulate a subject's eye during a test protocol according to the present invention. Optionally the number of field points 201, utilized with the system and method of the present application may vary from about 13 points to about 256 points or more, Optionally any number of points in a circular grid structure, about a visual field may be used to test specific areas of a subject's eye, for example a 64 point visual field map. Optionally the number of tested field point utilized is proportional to the required resolution of the filed map of the test protocol or the required test. Optionally each field ring 202, 204, 206, 208 is separated by about 10° degrees a 30° degree, another option is that each point within the ring is spaced and/or separated by at about 5° degrees resulting in higher resolution with more point of examination in the visual field.

Figure 3:
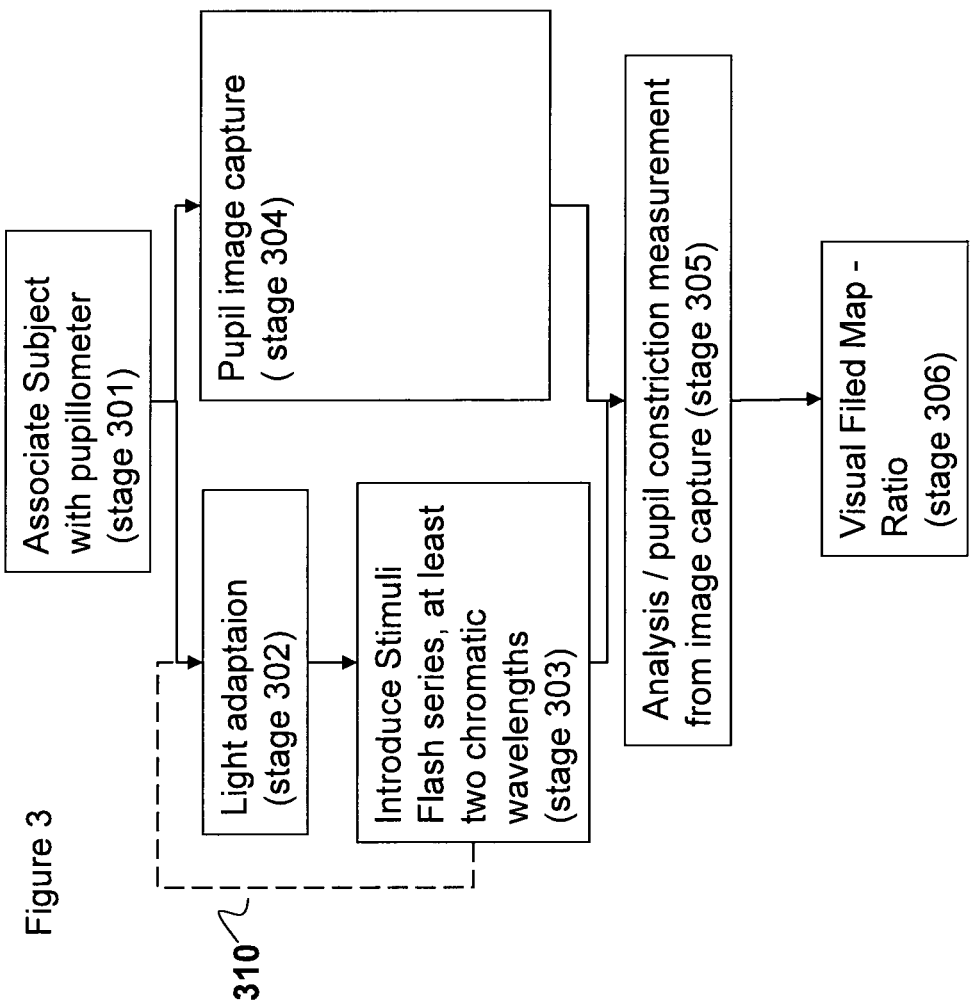
FIG. 3 is a flowcharts of an exemplary method according to the present invention.

FIG. 3 shows a flowchart of an exemplary method according to the present invention for objective chromatic perimetry analysis using pupillometer therein providing an objective, repeatable and quick test.

In stage 301, a subject is prepared for the test where at least one eye of a subject is introduced to pupillometer 100 wherein the subject's forehead and chin are supported by support frame 102 while the tested eye is focused onto focal fixation point marker 107 through at least one ocular 103. Optionally and preferably test preparation may include selecting the test sequence to be preformed via computer 109 utilizing dedicated software.

Most preferably testing sequence, comprising the stimulus parameters, the visual field points tested, tested eye(s), light adaptation and the number times a stimulus is presented or number of stimulus sessions, may be preset and automated according to the test being performed and/or according to the test's objectives. Optionally and preferably a testing sequence may be created manually, altered, changed, abstracted or otherwise controlled by an operator via dedicated software associated with computer 109 adapt at controlling pupillometer 100.

Most preferably stimulus parameters for example including but not limited to luminance, intensity, duration, and wavelength may be controlled by the operator via computer 109.

Optionally and preferably the visual field points stimulated (FIG. 2A-C) and the order and sequence by which they may be presented to a subject is automatically controlled or manually controlled via computer 109.

Optionally and preferably the number of stimuli provided at each of the visual field testing points may also be automated, manually or otherwise controlled via computer 109.

Optionally and preferably the test sequence and/or protocol may be performed on a single eye, on each eye individually one at a time, may alternate between both eyes, both eyes tested simultaneously, or any combination thereof. Optionally control of which eye is tested during the testing sequence is controlled via computer 109 and oculars 103. Optionally computer 109 provides for controlling oculars 103 according to the prescribed and/or selected testing sequence.

An objective chromatic perimetry test according to the present invention is initiated by simultaneously initiating and presenting a subject with stimulus as described in stage 303 below, while continuously capturing, recording and measuring a subject's PLR response to the presented stimuli in stages 304 and 305. Most preferably in stage 304 at least one or more camera 106 disposed within testing compartment 101 are simultaneously activated with the image capture and PLR analysis provided with computer 109.

In stage 302 following the pupillometer preparation and subject preparation, test compartment 101 is provided with a light adaptation where the background luminance, via light adaptation emitter 112 comprising at least one and up to three chromatic beam emitters 105c, of the test compartment is controlled and to facilitate and/or prime the eye for testing particular anatomical structures of the eye.

For example a background luminance of 2.7 cd/m$^2$ (candela per square meter) may be utilized to prime for testing of the rods, cones and ganglion. For example a background luminance equal to about 5 foot-lambert or 17.1 cd/m$^2$ (candela per square meter) may be utilized to specifically prime testing conditions for testing cones while suppressing rods. Most preferably light adaptation is provided throughout the test sequence and/or protocol.

Next in stage 303, the stimulus is provided to the tested eye and while camera 109 provides for capturing the images and video of subject's PLR. The stimulus and test sequence is preferably controlled with computer 109, and may be altered based on the type of test and test objective.

Optionally and preferably stimuli parameters are controllable for example including but not limited to wavelength, duration of stimulus, inter-stimuli delay, size, shape, luminance, intensity or the like parameters may be controlled with computer 109. Optionally test stimulus wavelength may be any chromatic beam from the visible spectrum spanning from about 390 nm to about 750 nm, for example including but not limited to violet range (about 380 nm to about 450 nm), blue range (about 450 nm to about 475 nm), cyan range (about 476 nm to about 495 nm), green range (about 495 nm to about 570 nm), yellow range (about 570 nm to about 590 nm), orange range (about 590 nm to about 620 nm), red range (about 620 nm to about 750 nm), in any combination thereof or the like. Optionally stimuli duration and/or delay may be from about 100 ms to about 4000 ms, for example including but not limited to about 100 m, about 200 ms, about 300 ms, about 400 ms, about 500 ms, about 600 ms, about 700 ms, about 800 ms, about 900 ms, about 1000 ms, about 1100 ms, about 1200 ms, about 1300 ms, about 1400 ms, about 1500 ms, about 1600 ms, about 1700 ms, about 1800 ms, about 1900 ms, about 2000 ms, about 2100 ms, about 2200 ms, about 2300 ms, about 2400 ms, about 2500 ms, about 2600 ms, about 2700 ms, about 2800 ms, about 2900 ms, about 3000 ms, about 3100 ms, about 3200 ms, about 3300 ms, about 3400 ms, about 3500 ms, about 3600 ms, about 3700 ms, about 3800 ms, about 3900 ms, about 4000 ms, or the like. Optionally stimuli luminance and/or intensity may be provided from about from $3.98 \times 10^{-8}$ cd/m$^2$ up to about $3.98 \times 10^2$ cd/m$^2$.

Optionally and preferably the test protocol and stimulus sequence may be presented to a subject in up to three sessions, optionally two sessions and most preferably at least one sessions, as shown with directional arrow 310.

Next following the completion of the test protocol where all stimuli have been presented over the specified visual field points to the tested eye and images of the PLR have been recorded (stage 304), in stage 305 and 306 a processor, optionally in the form of computer 109, may optionally provide a decision support device utilized to abstract the visual field map by determining a ratio of the PLR response of the second stimulus, long wavelength stimulus, in relation to the PLR response of the first stimuli, short wavelength stimulus. Most preferably PLR response is elucidated from video and image capture, provided by up to four cameras 106, utilized in stage 304 optionally with dedicated software adept at determining the pupil constriction and size. Most preferably the pupil constriction peak amplitude is then utilized to determine the PLR ratio per visual field points tested.

Most preferably the visual field map is determined in stage 306 is based on the recorded constriction results for each of the first and second stimuli to produce a PLR ratio of the long to short wavelengths ratio.

Optionally and preferably the resulting visual field map may be stored for later monitoring, decision support system diagnosis, and/or further processing.

Optionally any number of test protocol may be abstracted according to the method of the present invention where a ratio is used to evaluate individual visual field points for a number of animalize for example Glaucoma, RP, color blindness, color vision test or the like.

EXAMPLES

A preferred and optional embodiment of the present invention utilizing the method described in FIG. 3 utilizing system 120 of FIG. 1A-B and testing a visual field map comprising 13 visual field points, FIG. 2A, is described herein below with respect to Glaucoma and RP, in determining a ratio, namely red to blue. Test protocol comprising at least one and up to three stimuli sessions, as shown with directional arrow 310, wherein the stimuli comprises at least two wavelengths to stimulate at least 13 visual field points (FIG. 2A) to simulated each eye individually. Most preferably the wavelengths utilized comprise a first long wavelength chromatic beam, in the red range, and a second short wavelength chromatic beam, in the blue range. Optionally the first and second stimulus are presented in alternating fashion for each visual field points at the outermost 30° visual field ring 208 and sequentially toward the central filed ring 202.

Optionally and more preferably the first stimuli may be a short wavelength chromatic stimulus in the blue range, for example about 475 nm, while the second stimuli may be a long wavelength chromatic stimulus in the red range, for example about 650 nm. Optionally the first stimuli may be a long wavelength chromatic stimulus in the red range, for example about 650 nm, while the second stimuli may be a short wavelength chromatic stimulus in the blue range, for example about 475 nm.

Optionally and preferably the stimulus characteristics of the first stimuli is about 480±19 nm, duration of about 1 s (one second); inter-stimuli delay of about 1023 ms (milliseconds) and intensity of $3.98 \times 10^{-8}$ cd/m$^2$. Optionally and preferably the stimulus characteristics of the second stimuli is about 640±10 nm, duration of about 1 s (one second); inter-stimuli delay of about 891 ms (milliseconds) and intensity of $3.98 \times 10^{-8}$ cd/m$^2$.

The above test specification was utilized to determine the red/blue ratio of normal, RP and Glaucoma subjects to evaluate the system and method according to optional embodiments of the present invention.

Example 1

Normal Subjects

The system and method described in FIGS. 1-3 was tested on subjects having a healthy eye, in total 25 eyes from 14 subjects were tested, 6 females and 8 males, with a mean age 29.8 years. The stimulus provided as follows: first stimulus characteristics was a chromatic beam having a wavelength of 480±19 nm, duration of about 1 s (one second), provided three times; inter-stimuli delay of 1023 ms (milliseconds) and intensity of $3.98 \times 10^{-8}$ cd/m$^2$; and second stimulus characteristics was a chromatic beam having a wavelength of 640±10 nm, duration of about 1 s (one second); inter-stimuli delay of 891 ms (milliseconds) and intensity of $3.98 \times 10^{-8}$ cd/m$^2$.

Figure 4A:
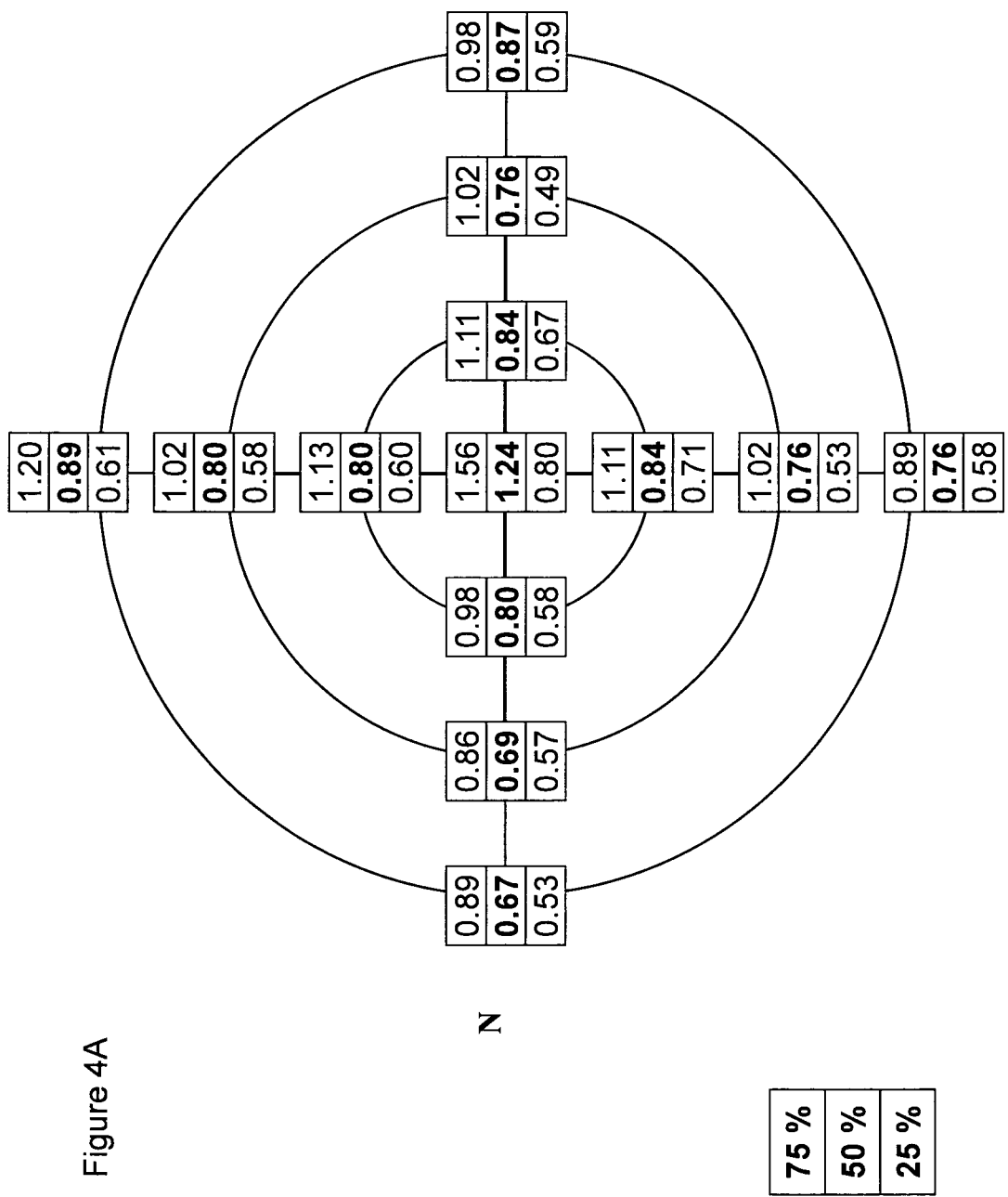
FIG. 4A-C are a schematic illustrative diagrams of a visual filed diagram showing of results obtained from health normal eyes within the 50th, 75th and 25th percentiles.
Figure 4B:
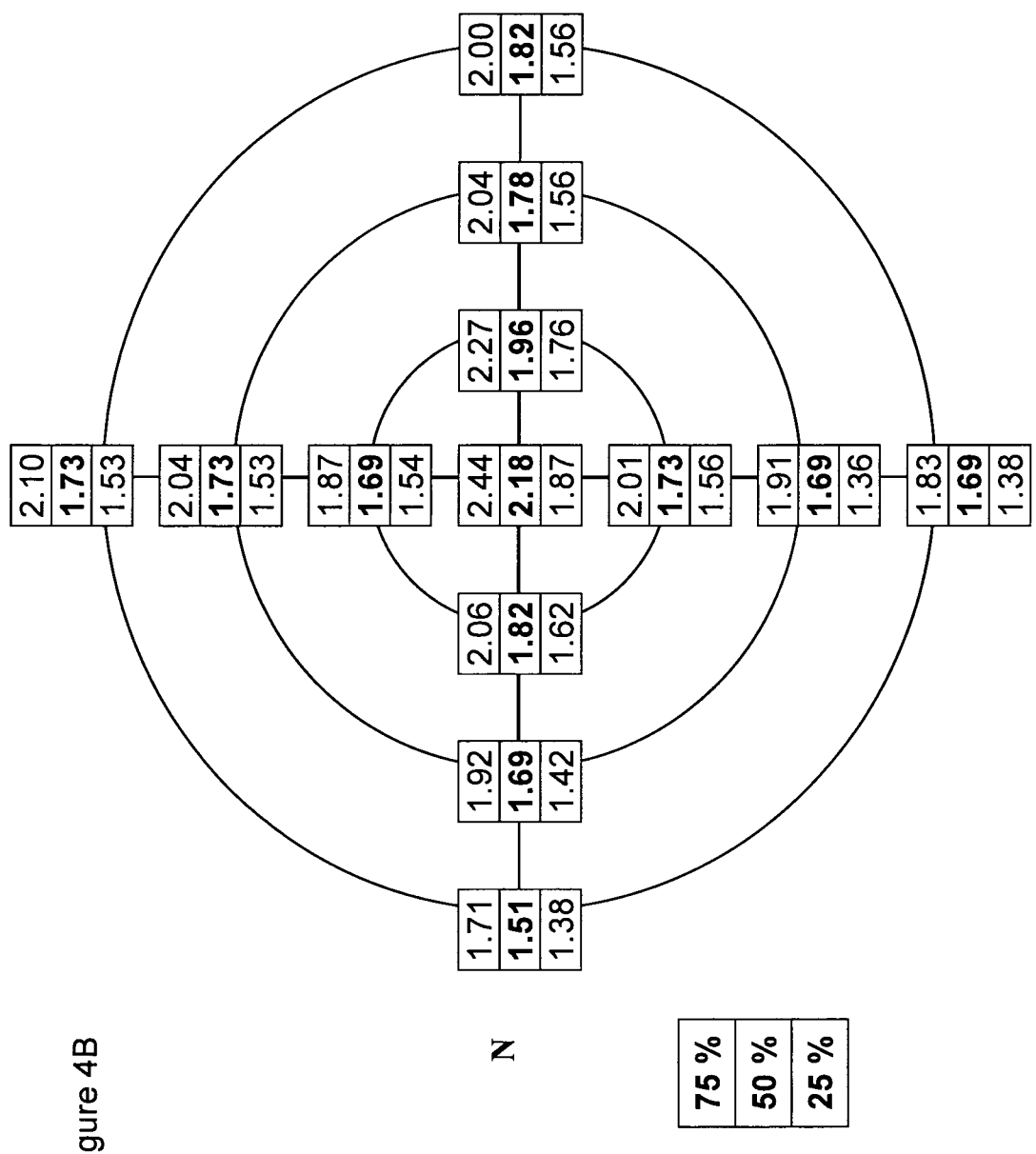

The visual field map was generated for both first and second stimuli, FIG. 4A shows the objective PLR response obtained with the second stimuli, while FIG. 4B shows the objective PLR response obtained with the first stimuli. Both FIGS. 4A and 4B show the respective population percentile score in 75$^{th}$ percentile, 50$^{th}$ percentile and 25$^{th}$ percentile.

Figure 4C:
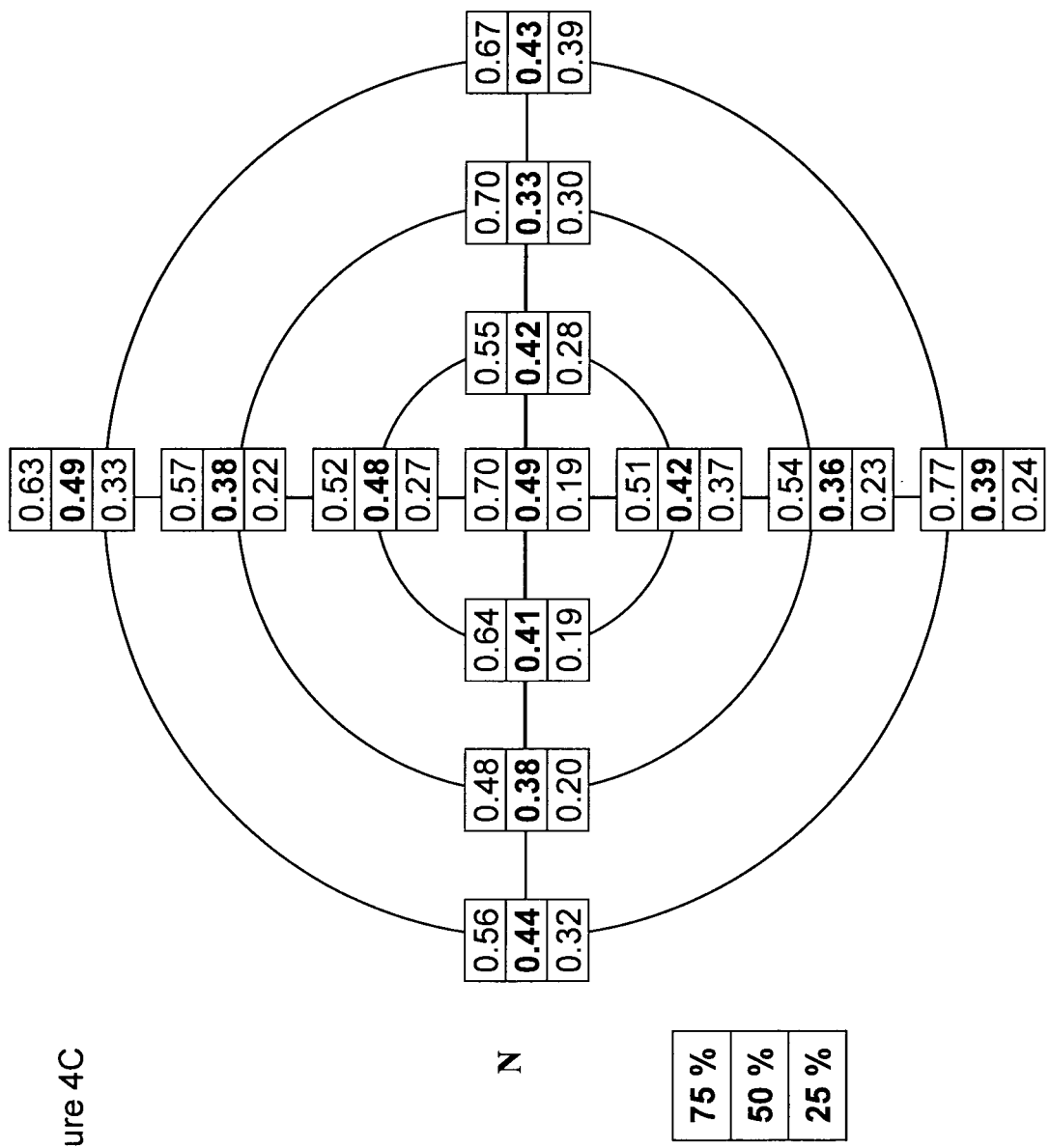

FIG. 4C shows the objective PLR response ratio obtained when comparing the response to the second stimuli with the response to the first stimuli. The visual filed map of FIG. 4C shows that the 50$^{th}$ percentile ratio is highest at the center of the visual filed is 0.5 and gradually reduces as the visual filed map extends to the 30° viewing angle. The results summarized and presented in Table 1 below:

TABLE 1

| | | Normal ratio. | | | |
|---|---|---|---|---|---|
| | | Nasal | Temporal | Up | Down |
| Normal | 0° | 0.5 | | | |
| | 10° | 0.41 | 0.45 | 0.48 | 0.43 |
| | 20° | 0.40 | 0.33 | 0.38 | 0.39 |
| | 30° | 0.5 | 0.44 | 0.5 | 0.4 |

The ratio obtained in Normal healthy eyes according to the system and method of the present application provides a basis to which individuals with damaged eyes may be compared with.

Example 2

Retinitis Pigmentosa Subjects

The system and method described in FIGS. 1-3 was tested on subjects with diagnosed Retinitis Pigmentosa ('RP'), in total 17 eyes were tested from 11 subjects, 4 female and 7 male, with a mean age of 34.3 years. The stimulus tested was as follows: first stimulus characteristics was a chromatic beam having a wavelength of 480±19 nm, duration of about 1 s (one second), provided three times; inter-stimuli delay of 1023 ms (milliseconds) and intensity of $3.98 \times 10^{-8}$ cd/m$^2$; and second stimulus characteristics was a chromatic beam having a wavelength of 640±10 nm, duration of about 1 s (one second); inter-stimuli delay of 891 ms (milliseconds) and intensity of $3.98 \times 10^{-8}$ cd/m$^2$.

Figure 5A:
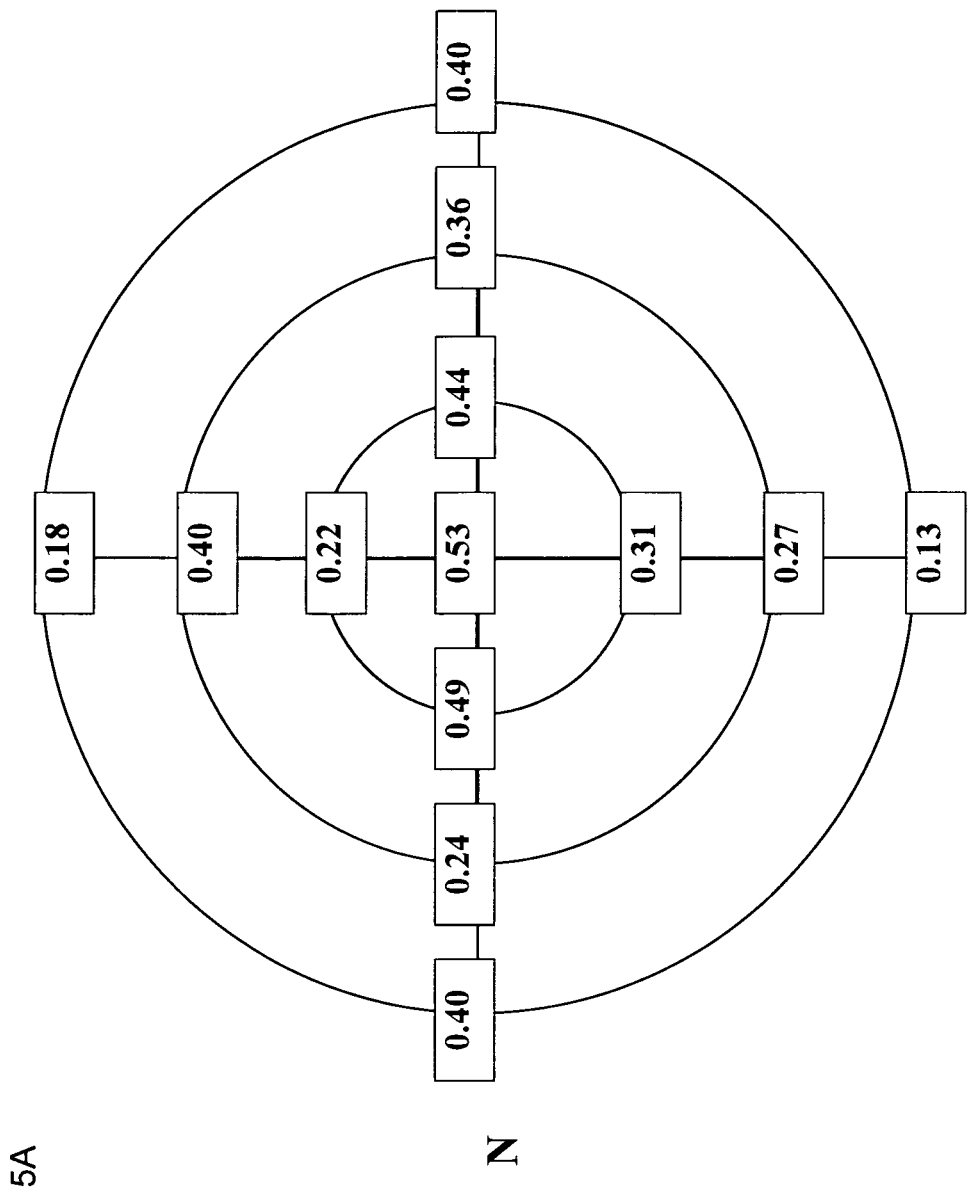
FIG. 5A-C are a schematic illustrative diagrams of a visual filed diagram showing of results obtained from subjects presenting with retinitis pigmentosa ('RP').
Figure 5B:
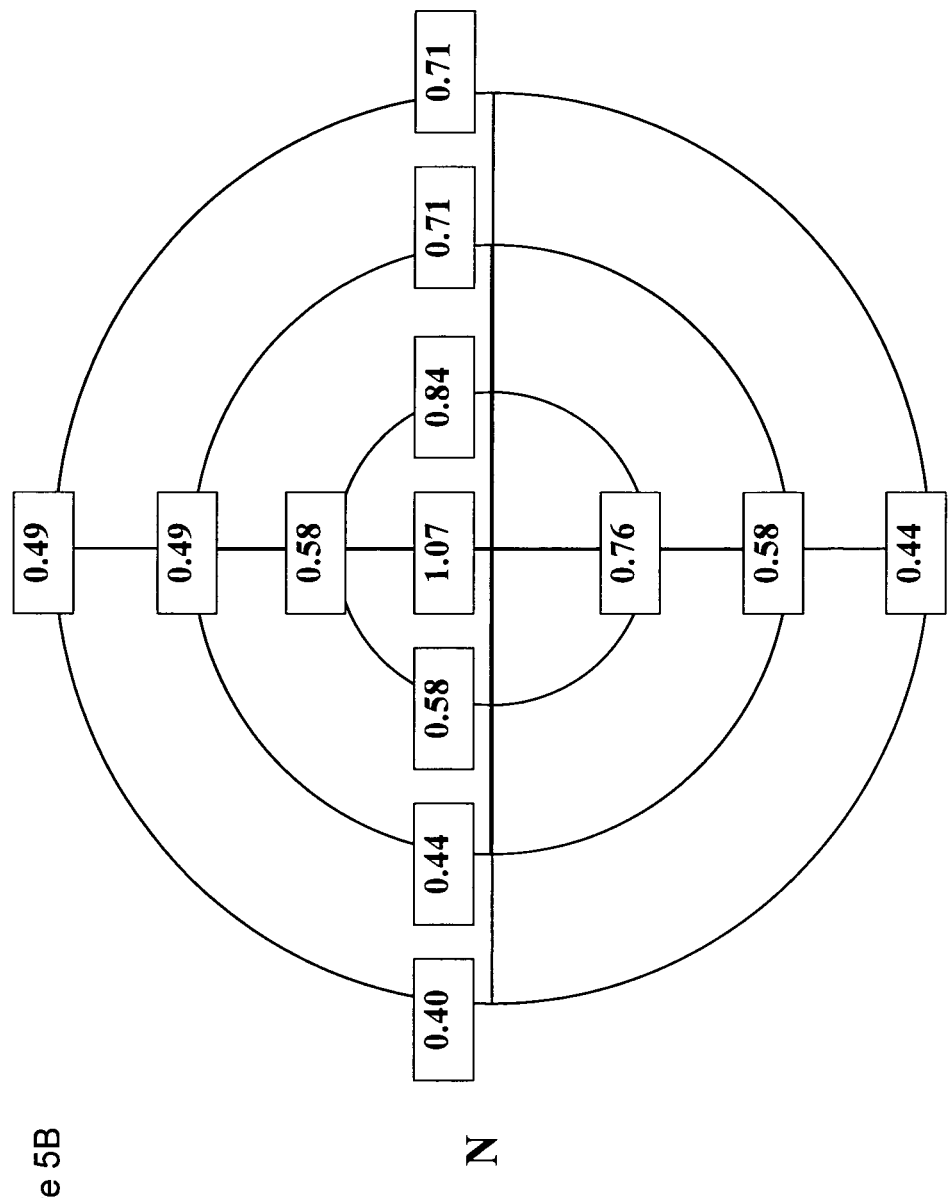
Figure 5C:
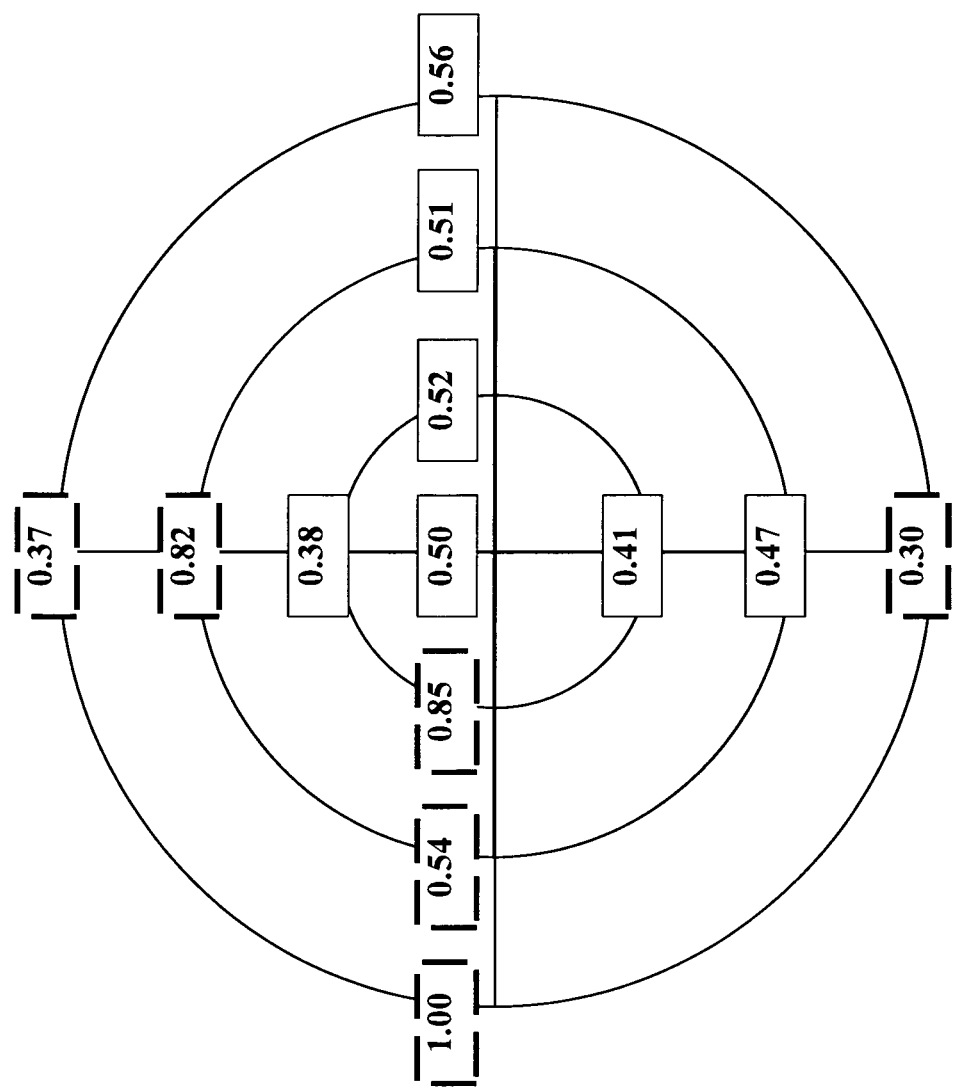

The visual field map was generated for both first and second stimuli in all subjects, an example taken from one subject is provide in FIGS. 5A-D. FIG. 5A shows the objective PLR response obtained with the second stimuli, while FIG. 5B shows the objective PLR response obtained with the first stimuli. The visual field maps obtained and displayed in FIGS. 5A-B were then utilized to calculate a ratio for the tested subject and displayed in FIG. 5C. A comparison of FIG. 5C for a subject diagnosed with RP with that of an otherwise health subject as shown in FIG. 5C clearly identifies the problem areas within the visual field, marked with a bold dashed line, that were shown to be significantly different from the measurement of the normal subjects. Therefore the ratio calculated according to the present invention provides a practitioner with the ability to identify the specific problematic areas within the visual field and possibly to isolate and provide treatment accordingly, not visible with the standard RP full field visual test.

Table 2 below provides a comparative table showing the visual field ratios results of subjects with normal visions versus those diagnosed with RP.

TABLE 2

Normal ratio vs. RP ratio.

|  |  | Nasal | Temporal | Up | Down |
|---|---|---|---|---|---|
| Normal | 0° | 0.5 |  |  |  |
|  | 10° | 0.41 | 0.45 | 0.48 | 0.43 |
|  | 20° | 0.40 | 0.33 | 0.38 | 0.39 |
|  | 30° | 0.5 | 0.44 | 0.5 | 0.4 |
| RP | 0° | 0.5 |  |  |  |
|  | 10° | 0.52 | 0.54 | 0.56 | 0.59 |
|  | 20° | 0.53 | 0.62 | 0.71 | 0.42 |
|  | 30° | 0.69 | 0.64 | 0.54 | 0.91 |

The utility in adapting the ratio provided by the system and method of the present invention as a test for diagnosing subjects with RP is provided in Table 3 below, showing that specificity and sensitivity of the objective ratio test produces promising results.

TABLE 3

Sensitivity and Specificity of Ratio test of Normal vs. RP subjects

|  |  | Subjective VF | |
|---|---|---|---|
| Red/Blue |  | Positive | Negative |
| Pupillometer | Positive | 56 | 14 |
| Based VF | Negative | 15 | 58 |
|  |  | Sensitivity = 78.9% | Specificity = 80.5% |

The average of the PLR ratio in the normal subjects was 0.41+/−0.2 (Average+SD). The average of the PLR ratio measurements of the patients in the seeing area of the visual fields was 0.62+/−0.25 and in the non-seeing area 0.97+0.2. The PLR ratio was significantly different between the normal subject and the RP patients and between seeing areas and non-seeing areas in the visual fields of the RP patients (ANOVA, p<0.001).

Example 2

Glaucoma Patient

The system and method described in FIGS. 1-3 was tested on subjects with diagnosed Glaucoma, in total 5 eyes were tested from 3 subjects, 1 female and 2 male, with a mean age of 66.5 years. The stimulus tested was as follows: first stimulus characteristics was a chromatic beam having a wavelength of 480±19 nm, duration of about 1 s (one second), provided three times; inter-stimuli delay of 1023 ms (milliseconds) and intensity of $3.98 \times 10^{-8}$ cd/m$^2$; and second stimulus characteristics was a chromatic beam having a wavelength of 640±10 nm, duration of about 1 s (one second); inter-stimuli delay of 891 ms (milliseconds) and intensity of $3.98 \times 10^{-8}$ cd/m$^2$.

Figure 6A:
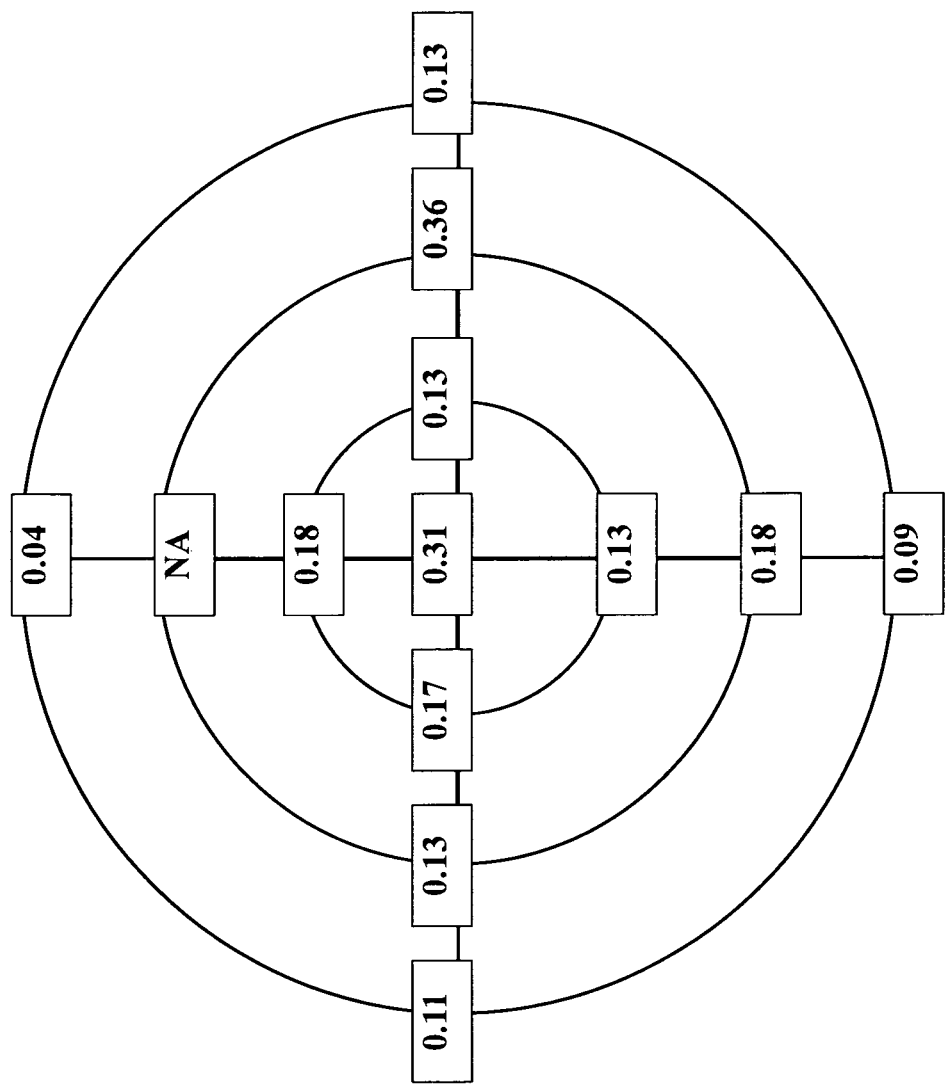
FIG. 6A-D are a schematic illustrative diagrams of a visual filed diagram showing of results obtained from subjects presenting with glaucoma.
Figure 6B:
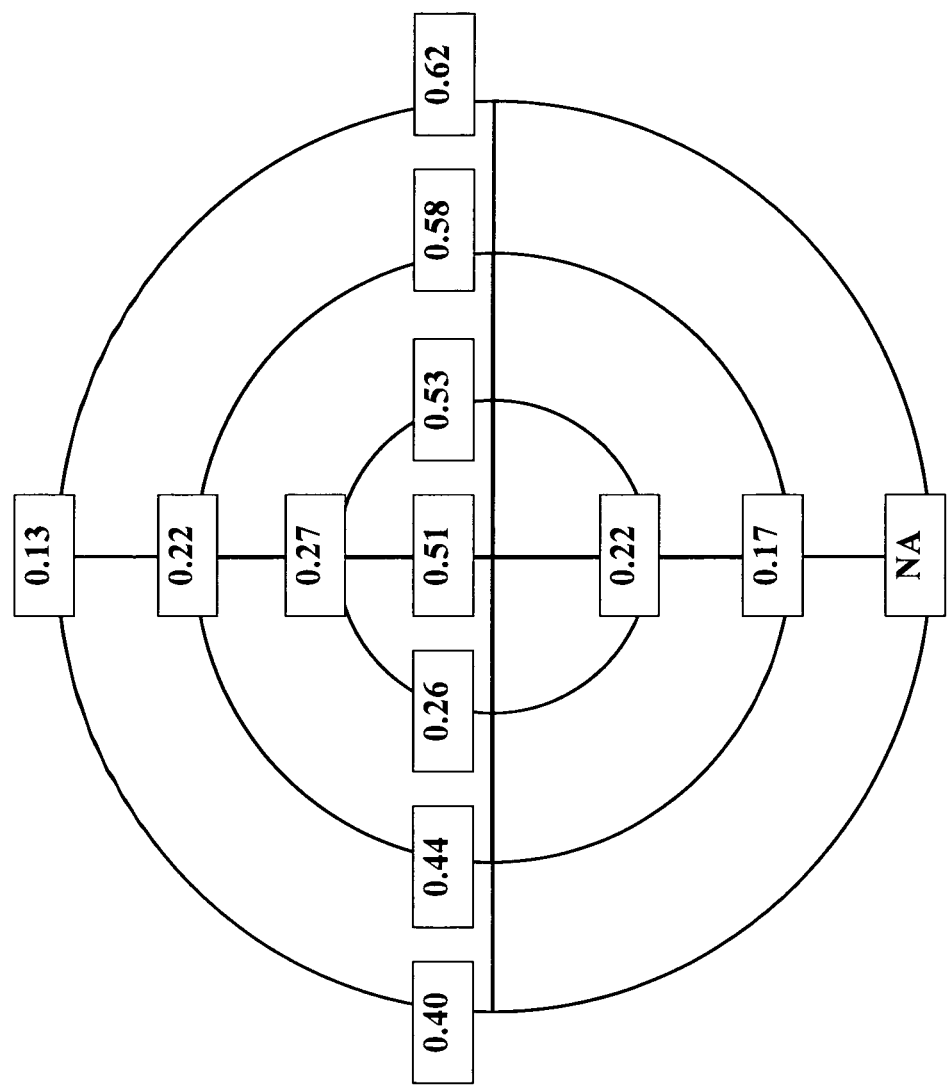
Figure 6C:
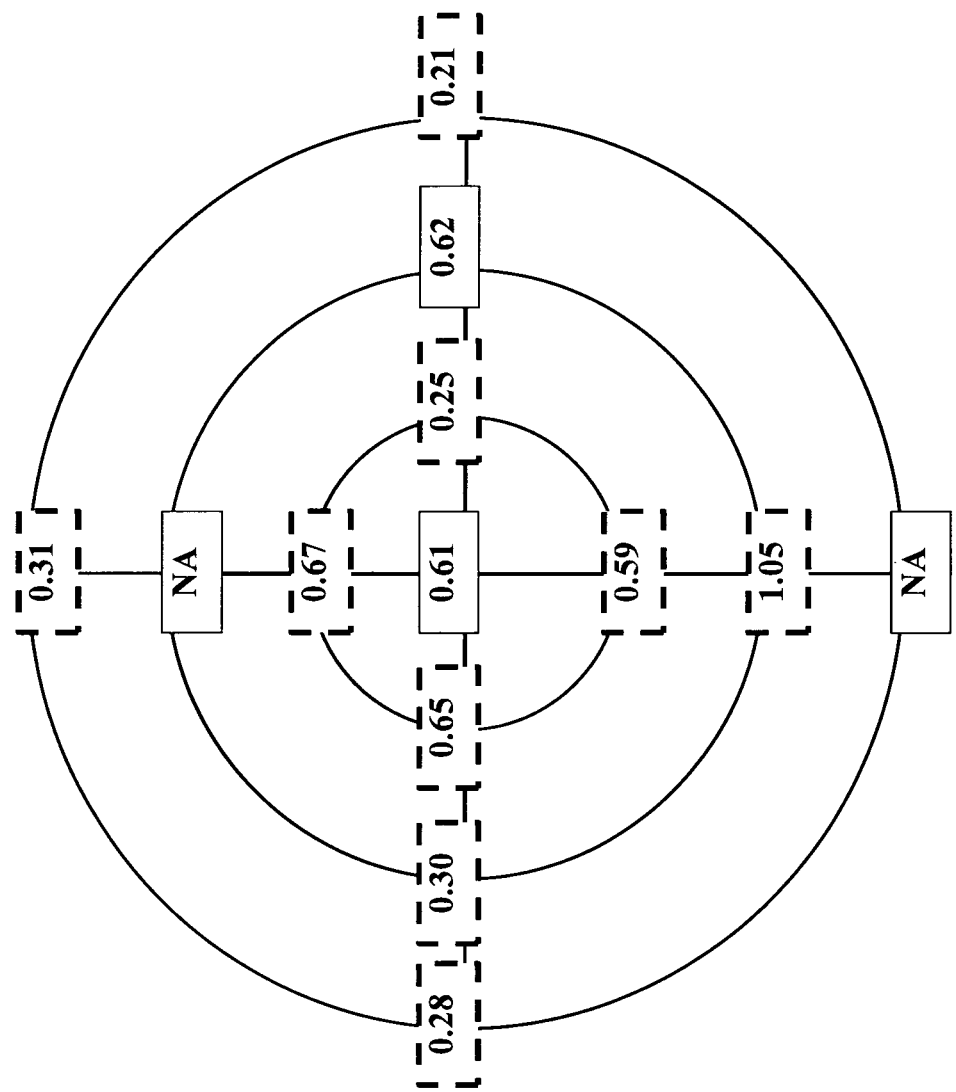

The visual field map was generated for both first and second stimuli in all subjects, an example taken from one subject is provided in FIGS. 6A-D. FIG. 6A shows the objective PLR response obtained with the second stimuli, while FIG. 6B shows the objective PLR response obtained with the first stimuli. The visual field maps obtained and displayed in FIGS. 6A-B were then utilized to calculate a ratio for the tested subject and displayed in FIG. 6C. A comparison of FIG. 6C for a subject diagnosed with Glaucoma with that of an otherwise health subject as shown in FIG. 6C clearly identifies the problem areas within the visual field, marked with a bold dashed line, that were shown to be significantly different from the measurement of the normal subjects, FIG. 4C. Therefore the ratio calculated according to the present invention provides a practitioner with the ability to identify the specific problematic areas within the visual field and possibly to isolate and provide treatment accordingly.

Figure 6D:
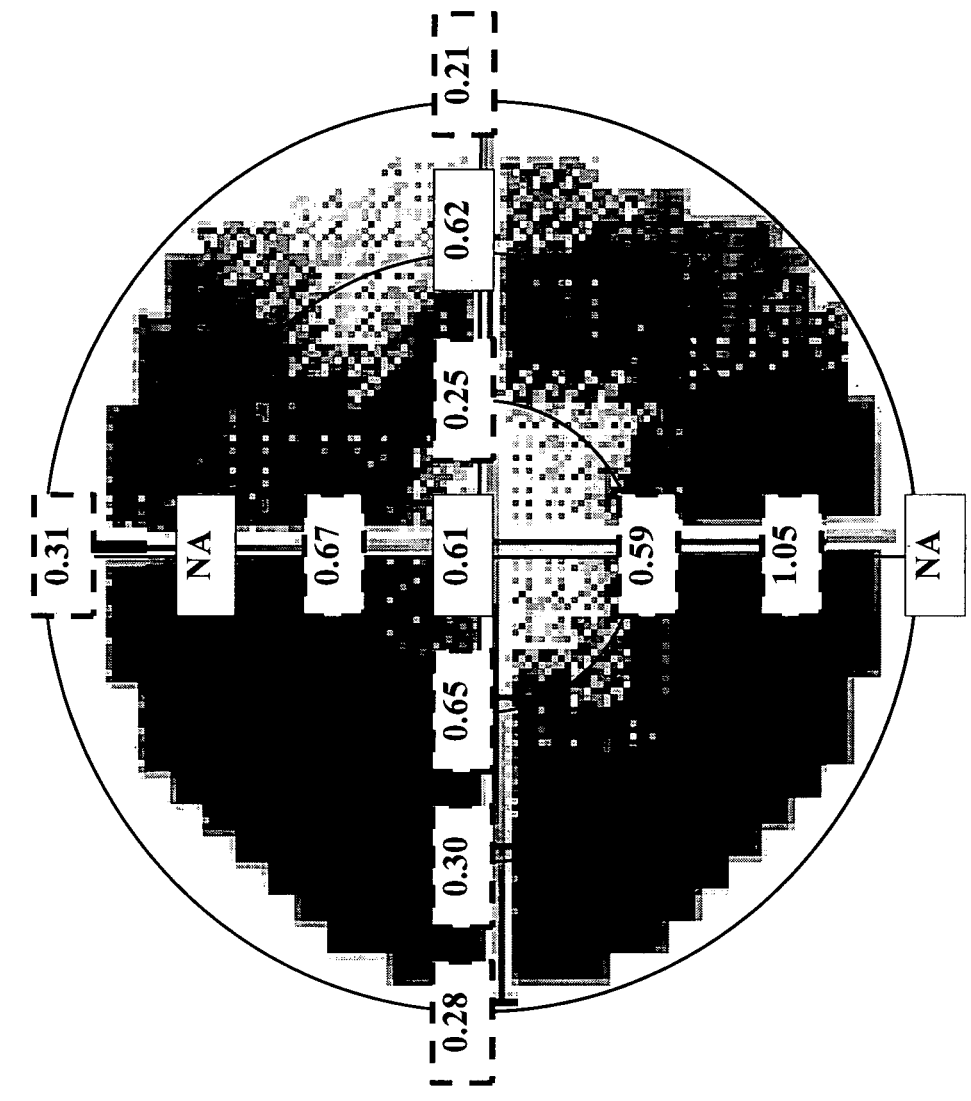

FIG. 6D provides a comparative depictions showing the visual filed map independently obtained from a glaucoma subject superimposed with the ratio determined according the system and method of the present invention as shown in FIG. 6C. The glaucoma subject's visual map provided by the gold standard test, is provided as a grayscale image depicting visual sensitivities of the retina in shades of gray. Areas of very poor retinal sensitivity are darkly shaded, and areas of good retinal sensitivity are lightly shaded. The superimposed images, FIG. 6D, of the two methods shows that areas where the ratio is significantly different from the norm is indicative of a problem areas as the visual maps correspond to one another. Specifically the lightly shaded area indicating good retinal sensitivity is paralleled in that the ratio determined for those visual filed spots is within the norm.

Accordingly, the method and system for determining the ratio of a long wavelength chromatic stimuli to a short wavelength chromatic stimuli provides an improved way of diagnosing and elucidating an underlying problem within the eye anatomy, that provides a method for subjectively testing at least one eye.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. A method for determining the state of health of an eye using a pupillometer to provide an objective chromatic perimetry analysis test, wherein:
the pupillometer comprises a processor, at least one camera, and a testing compartment provided in the form of a substantially hemispheric bowl;
the substantially hemispheric bowl comprises a plurality of chromatic beam emitters arranged about a visual field forming a plurality of visual field testing points;
the chromatic beam emitters generate a plurality of chromatic stimuli about the visual field testing points;
the chromatic stimuli comprise a first chromatic beam stimulus and a second chromatic beam stimulus;
at least one of the first chromatic beam stimulus and the second chromatic beam stimulus employs a wavelength that stimulates ganglion cells;
the testing compartment further comprises a light adaptation emitter;
the inner surface further comprises a fixation point opposite a subject's line of sight;
the at least one camera records pupil contraction in response to the first and second chromatic beam stimuli;
the processor controls the chromatic beam emitters and the stimulus parameters of the chromatic beam emitters;
the processor processes data associated with and generated by the first and second chromatic beam stimuli and the camera; and
the method comprises
generating quantitative pupillary light reflex (PLR) measurements of a pupillary light reflex (PLR) in response to chromatic beam stimuli presented at the plurality of visual field testing points,
determining ratios of the quantitative PLR measurements at the plurality of visual field testing points, wherein each of the ratios at each testing point represents a quantitative PLR measurement at the first chromatic beam stimulus relative to a quantitative PLR measurement at the second chromatic beam stimulus, and
determining the state of health of the eye utilizing the ratios,
wherein (i) the first chromatic beam stimulus employs a shorter-wavelength chromatic beam, relative to the second chromatic beam stimulus, (ii) the second chromatic beam stimulus employs a longer-wavelength chromatic beam, relative to the first chromatic beam stimulus, and (iii) the wavelengths of the first chromatic beam stimulus and the second chromatic beam stimulus are selected from the visual spectrum spanning from about 390 nm to about 750 nm.

2. The method of claim 1, further comprising a controllable shutter for controlling the size and/or shape of the generated stimulus.

3. The method of claim 2, wherein the shutter size corresponds to a stimulus having a substantially circular formation with a diameter from about 0.8 cm to about 2 cm.

4. The method of claim 1, wherein the at least one camera comprises two or more cameras for recording a pupillary light reflex (PLR) of at least one tested eye.

5. The method of claim 4, wherein the PLR is recorded for each eye using the two or more cameras.

6. The method of claim 1, wherein the ratios characterize PLR measured based on the response to the longer-wavelength stimulus relative to PLR measured based on the response to the shorter-wavelength stimulus.

7. The method of claim 1, wherein each of the first chromatic beam stimulus and the second chromatic beam stimulus stimulates a specific anatomical structure of the eye.

8. The method of claim 1, wherein the first chromatic beam stimulus stimulates rods and ganglion cells, and the second chromatic beam stimulus stimulates cones.

9. The method of claim 1, wherein the first chromatic beam stimulus and the second chromatic beam stimulus stimulate at least one different anatomical structure of the eye from one another.

10. The method of claim 1, wherein:
the first and second chromatic beam stimuli are provided for a duration of between about 0.1 seconds to about 4 seconds, with
an intensity of between about $3.98 \times 10^{-8}$ cd/m$^2$ to about $3.98 \times 10^2$ cd/m$^2$.

11. The method of claim 1, wherein the ratios are mapped to a visual field map.

12. The method of claim 1, wherein the ratios are indicative of the state of health of anatomical structures correlated with individual visual field points.

13. The method of claim 1, wherein the ratios are indicative of underlying normal and/or healthy anatomical structures is provided by one or more of the following field point coordinates and expected ratio (0°, nasal, 0.50); (10°, nasal, 0.41); (10°, temporal, 0.45); (10°, up, 0.48); (10°, down, 0.43); (20°, nasal, 0.40); (20°, temporal, 0.33); (20°, up, 0.38); (20°, down, 0.39); (30°, nasal, 0.50); (30°, temporal, 0.44); (30°, up, 0.5); (30°, down, 0.40).

14. The method of claim 1, wherein the ratios are indicative of the state of health of an eye associated with glaucoma, and retinitis pigmentosa.

15. The method of claim 1, wherein the ratios are indicative of the state of health of an eye associated with color blindness.

16. The method of claim 1, wherein the test is performed with background luminance providing for light adaptation.

17. The method of claim 16, wherein the background luminance is 2.7 cd/m$^2$.

18. The method of claim 16, wherein the background luminance is controlled and provided to facilitate testing of an anatomical structure of the eye.

19. The method of claim 16, wherein the background luminance is from about 1 cd/m$^2$ to about 20 cd/m$^2$.

20. The method of claim 16, wherein the light adaptation is provided at different controllable periods of the test.

21. The method of claim 16, wherein the different controllable periods of the test are selected from the group consisting of: between stimulus presentations, between visual field testing points, between visual field rings, and a combination of one or more of the foregoing.

22. The method of claim 16, wherein the background luminance is 17.1 cd/m$^2$.

23. The method of claim 1, wherein the quantitative measurement of the PLR comprises pupil constriction amplitude.

24. The method of claim 1, wherein the quantitative measurement of the PLR comprises pupil constriction latency.

25. The method of claim 1, wherein the first stimulus is within the blue range from about 450 nm to about 490 nm and the second stimulus is within the red range from about 635 nm to about 700 nm.

26. The method of claim 1, wherein the first stimulus is within the blue range from about 475 nm to about 485 nm and the second stimulus is within the red range from about 620 nm to about 630 nm.

27. The method of claim 1, wherein either the first stimulus or the second stimulus is within the green range from about 495 nm to about 570 nm.

28. The method of claim 1, wherein each chromatic beam emitter is specific to a particular chromatic stimulus source.

29. A method for determining the state of health of an eye using a pupillometer to provide an objective chromatic perimetry analysis test, wherein:
   the pupillometer comprises a processor, at least one camera, and a testing compartment;
   the testing compartment comprises a plurality of chromatic beam emitters arranged about a visual field forming a plurality of visual field testing points, a light adaptation emitter, and an inner surface comprising a fixation point opposite a subject's line of sight;
   the chromatic beam emitters generate a plurality of chromatic stimuli about the visual field testing points;
   the chromatic stimuli comprise a first chromatic beam stimulus and a second chromatic beam stimulus at least one of the first chromatic beam stimulus and the second chromatic beam stimulus employs a wavelength that stimulates ganglion cells;
   the at least one camera records pupil contraction in response to the first and second chromatic beam stimuli;
   the processor controls the chromatic beam emitters and the stimulus parameters of the chromatic beam emitters;
   the processor processes data associated with and generated by the first and second chromatic beam stimuli and the camera; and
   the method comprises
      generating quantitative pupillary light reflex (PLR) measurements of a pupillary light reflex (PLR) in response to chromatic beam stimuli presented at the plurality of visual field testing points,
      determining ratios of the quantitative PLR measurements at the plurality of visual field testing points, wherein each of the ratios at each testing point represents a quantitative PLR measurement at the first chromatic beam stimulus relative to a quantitative PLR measurement at the second chromatic beam stimulus, and
      determining the state of health of the eye utilizing the ratios, wherein (i) the first chromatic beam stimulus employs a shorter-wavelength chromatic beam, relative to the second chromatic beam stimulus, (ii) the second chromatic beam stimulus employs a longer-wavelength chromatic beam, relative to the first chromatic beam stimulus, and (iii) the wavelengths of the first chromatic beam stimulus and the second chromatic beam stimulus are selected from the visual spectrum spanning from about 390 nm to about 750 nm.

* * * * *